(12) United States Patent
Whayne et al.

(10) Patent No.: US 7,063,682 B1
(45) Date of Patent: Jun. 20, 2006

(54) CATHETER DISTAL ASSEMBLY WITH PULL WIRES

(75) Inventors: James G. Whayne, Saratoga, CA (US); Sidney D. Fleischman, Menlo Park, CA (US)

(73) Assignee: EP Technologies, Inc., San Jose, CA (US)

( * ) Notice: Subject to any disclaimer, the term of this patent is extended or adjusted under 35 U.S.C. 154(b) by 0 days.

(21) Appl. No.: 09/507,613

(22) Filed: Feb. 21, 2000

Related U.S. Application Data

(63) Continuation of application No. 08/961,374, filed on Oct. 30, 1997, now Pat. No. 6,203,525, which is a continuation-in-part of application No. 08/769,856, filed on Dec. 19, 1996, now Pat. No. 6,332,880.

(51) Int. Cl.
*A61D 37/00* (2006.01)

(52) U.S. Cl. .............................. 604/95.04; 604/95.01; 600/372; 600/146; 606/41; 607/122; 607/101

(58) Field of Classification Search ............. 604/95.01, 604/528, 95.04; 600/372–374, 146–149; 606/41; 607/122, 100–102
See application file for complete search history.

(56) References Cited

U.S. PATENT DOCUMENTS

| | | |
|---|---|---|
| 1,207,479 A | 12/1916 | Bisgaard |
| 4,033,331 A | 7/1977 | Guss et al. |
| 4,181,131 A | 1/1980 | Ogiu |
| 4,245,624 A | 1/1981 | Komiya |
| 4,753,223 A | 6/1988 | Bremer |
| 4,826,087 A | 5/1989 | Chinery |
| 5,041,085 A | 8/1991 | Osborne |
| 5,098,412 A | 3/1992 | Shiu |
| 5,156,151 A | 10/1992 | Imran |
| 5,263,493 A | 11/1993 | Avitall |
| 5,273,535 A | 12/1993 | Edwards |
| 5,306,245 A | 4/1994 | Heaven |
| 5,368,592 A | 11/1994 | Stern |
| 5,370,675 A | 12/1994 | Edwards |
| 5,399,165 A | 3/1995 | Paul, Jr. |
| 5,415,656 A | 5/1995 | Tohon et al. |
| 5,437,665 A | 8/1995 | Munro |
| 5,439,006 A | 8/1995 | Brennen |
| 5,472,017 A | 12/1995 | Kovalcheck |
| 5,482,037 A | 1/1996 | Borghi |
| 5,487,385 A | 1/1996 | Avitall |
| 5,487,757 A | 1/1996 | Truckai |
| 5,500,012 A | 3/1996 | Brucker |
| 5,549,661 A | 8/1996 | Kordis |

(Continued)

FOREIGN PATENT DOCUMENTS

DE  3920707 A1  1/1991

(Continued)

*Primary Examiner*—Cris Rodriguez
(74) *Attorney, Agent, or Firm*—Henricks, Slavin & Holmes LLP

(57) ABSTRACT

A catheter assembly having a sheath, which includes a side wall enclosing an interior bore, and a distal region. The assembly also has a bendable catheter tube, which is carried for sliding movement in the interior bore. A pull wire also runs through the interior bore of the sheath, preferably within a lumen. The catheter tube has a distal portion with a coupling which joins the distal portion of the catheter tube and the distal portion of the pull wire. Relative movement of the pull wire and the sheath causes bending of the catheter tube outwardly through the opening, in response to sliding movement of the catheter tube within the interior bore toward the distal region of the sheath.

28 Claims, 23 Drawing Sheets

U.S. PATENT DOCUMENTS

| | | |
|---|---|---|
| 5,571,088 A | 11/1996 | Lennox et al. |
| 5,637,090 A | 6/1997 | McGee |
| 5,642,736 A | 7/1997 | Avitall |
| 5,672,174 A | 9/1997 | Gough |
| 5,702,368 A | 12/1997 | Stevens |
| 5,702,438 A | 12/1997 | Avitall |
| 5,709,224 A | 1/1998 | Behl |
| 5,730,127 A | 3/1998 | Avitall |
| 5,738,683 A | 4/1998 | Osypka |
| 5,782,899 A | 7/1998 | Imran |
| 5,800,482 A | 9/1998 | Pomeranz |
| 5,800,484 A | 9/1998 | Gough |
| 5,820,591 A | 10/1998 | Thompson |
| 5,836,947 A | 11/1998 | Fleischman |
| 5,863,291 A | 1/1999 | Schaer |
| 5,865,800 A | 2/1999 | Mirarchi |
| 5,879,295 A | 3/1999 | Li et al. |
| 5,895,417 A | 4/1999 | Pomeranz |
| 5,910,129 A | 6/1999 | Koblish |
| 5,931,811 A | 8/1999 | Haissaguerre |
| 5,938,660 A | 8/1999 | Swartz |
| 5,971,983 A | 10/1999 | Lesh |
| 6,012,457 A | 1/2000 | Lesh |
| 6,013,052 A | 1/2000 | Durman |
| 6,016,811 A | 1/2000 | Knopp |
| 6,027,473 A | 2/2000 | Ponzi |
| 6,048,329 A | 4/2000 | Thompson |
| 6,064,902 A | 5/2000 | Haissaguerre |
| 6,071,274 A | 6/2000 | Thompson |
| 6,071,279 A | 6/2000 | Whayne |
| 6,120,500 A | 9/2000 | Bednarek |
| 6,203,525 B1 | 3/2001 | Whayne |
| 6,237,605 B1 | 5/2001 | Vaska |
| 6,311,692 B1 | 11/2001 | Vaska |
| 6,314,962 B1 | 11/2001 | Vaska |
| 6,314,963 B1 | 11/2001 | Vaska |
| 6,332,880 B1 | 12/2001 | Yang |
| 6,402,746 B1 | 6/2002 | Whayne |
| 6,412,476 B1 | 7/2002 | Thompson et al. |
| 6,454,758 B1 | 9/2002 | Thompson |
| 6,464,700 B1 | 10/2002 | Koblish |
| 6,607,505 B1 | 8/2003 | Thompson et al. |

FOREIGN PATENT DOCUMENTS

| | | |
|---|---|---|
| EP | 0238106 A1 | 9/1987 |
| EP | 0737487 A2 | 10/1996 |
| EP | 0868922 A2 | 10/1998 |
| EP | 0916360 A2 | 5/1999 |
| WO | WO95/10322 | 4/1995 |
| WO | WO97/37607 | 10/1997 |
| WO | WO97/42966 | 11/1997 |
| WO | WO98/26724 | 6/1998 |
| WO | WO99/18878 | 4/1999 |

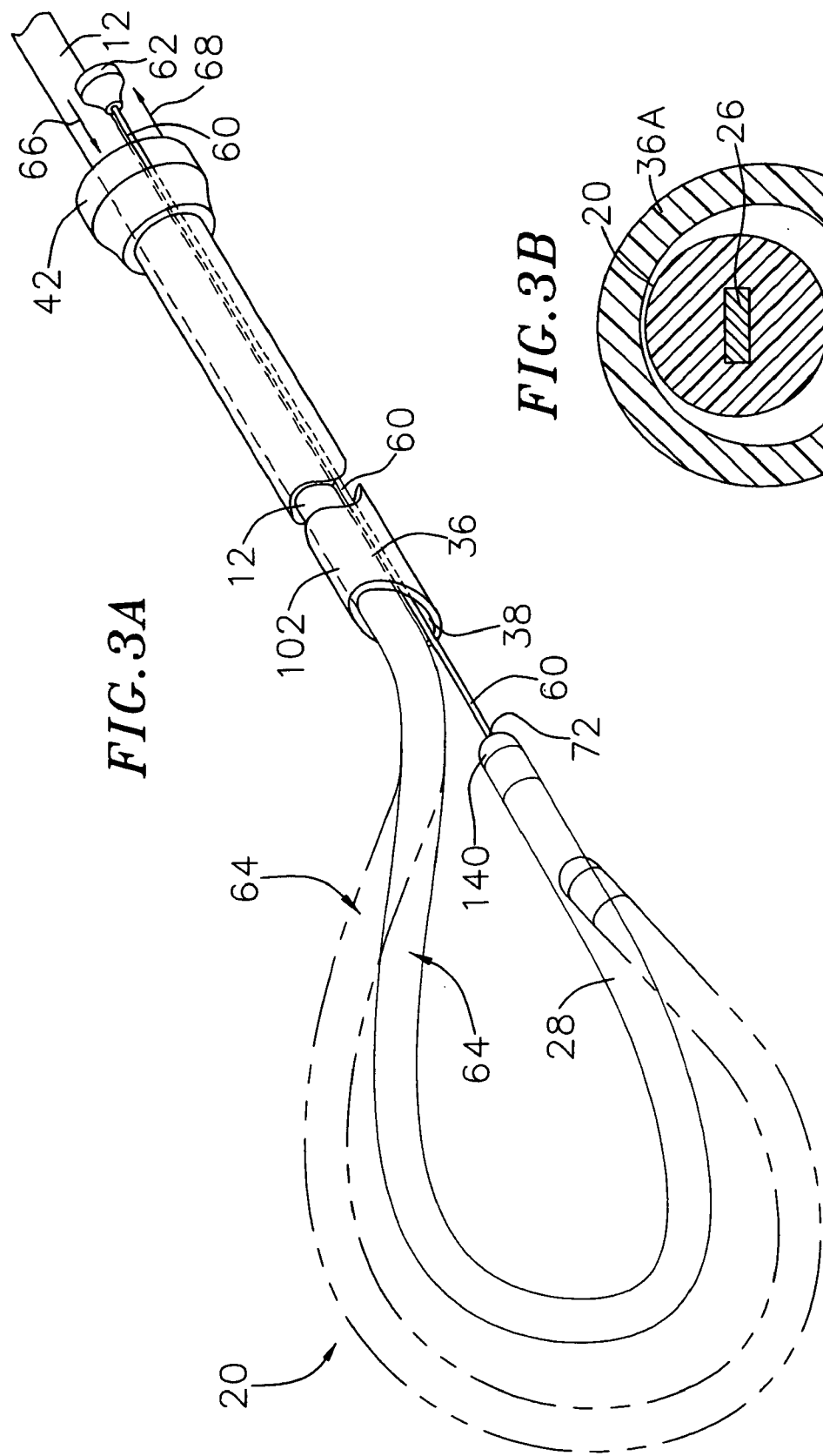
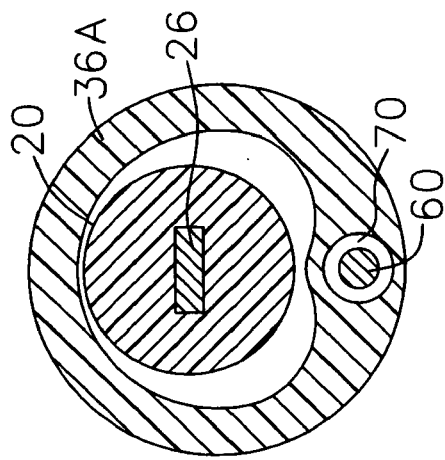

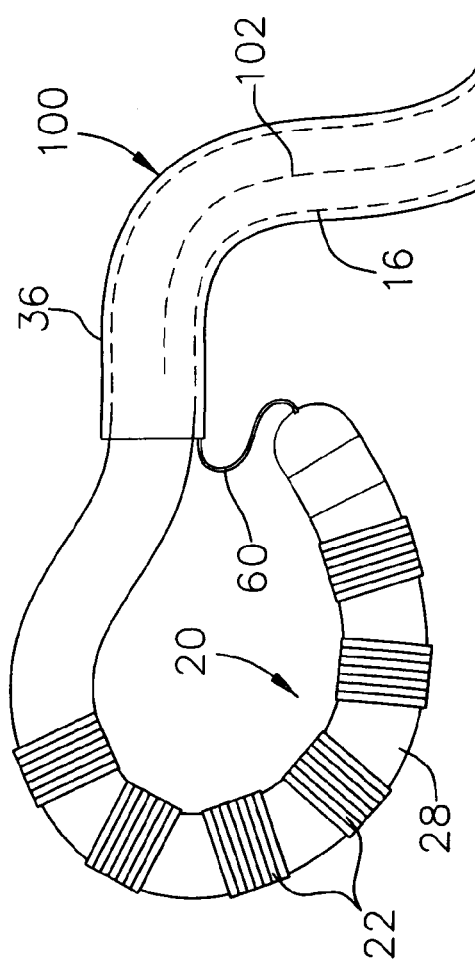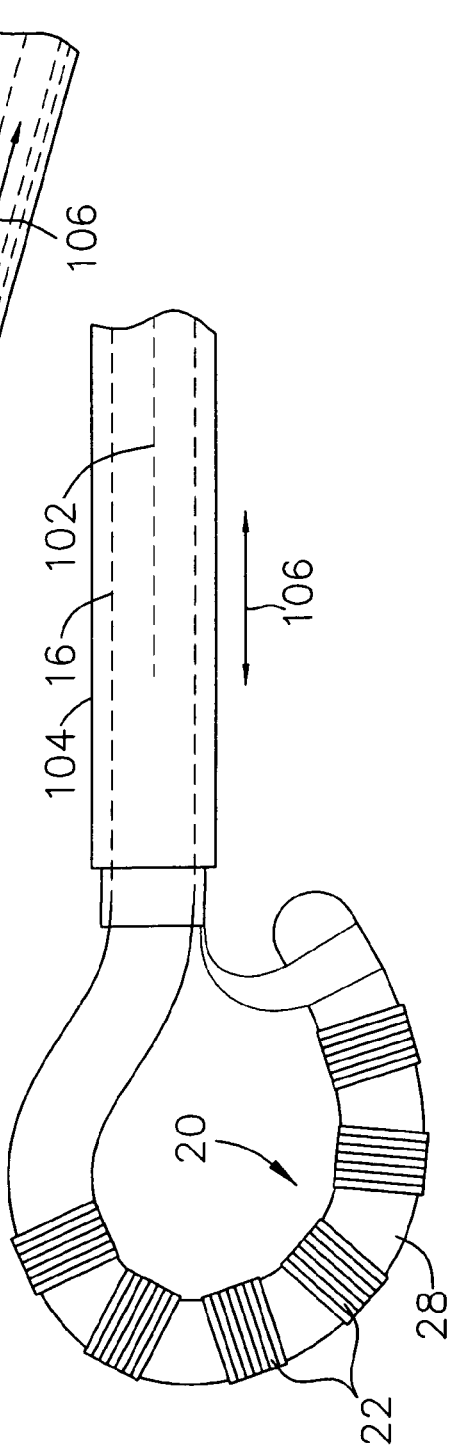

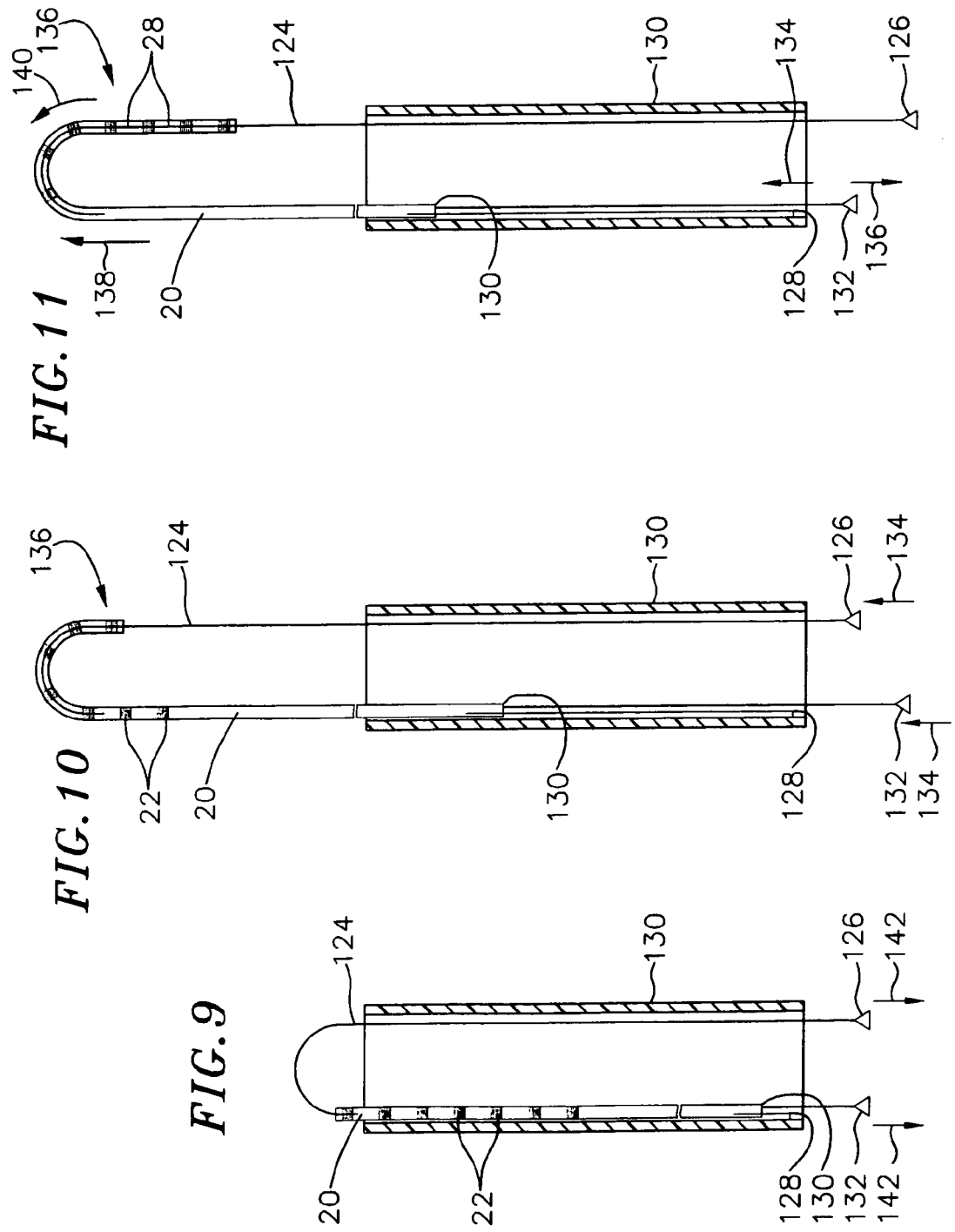

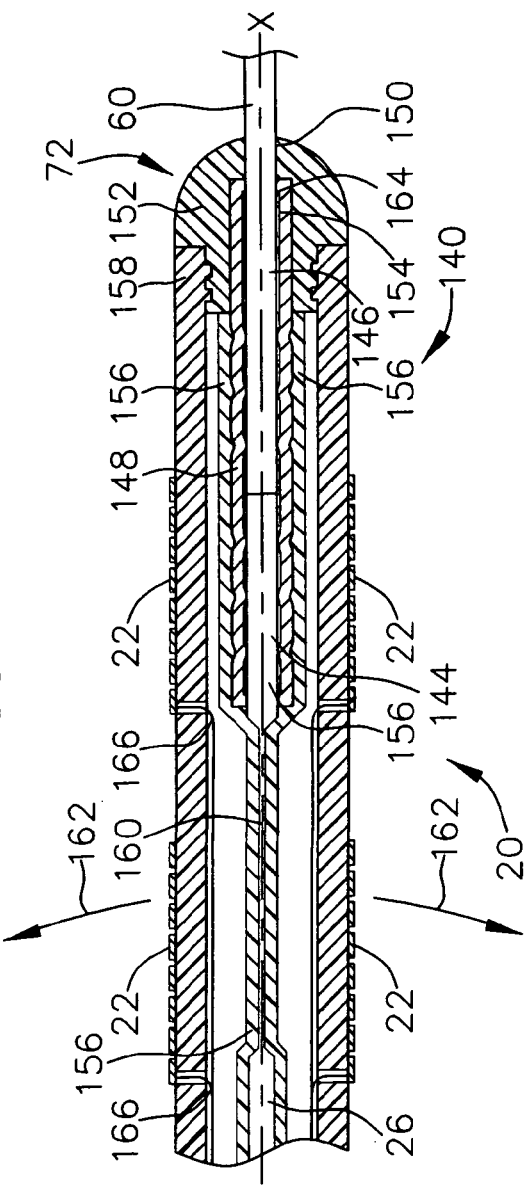
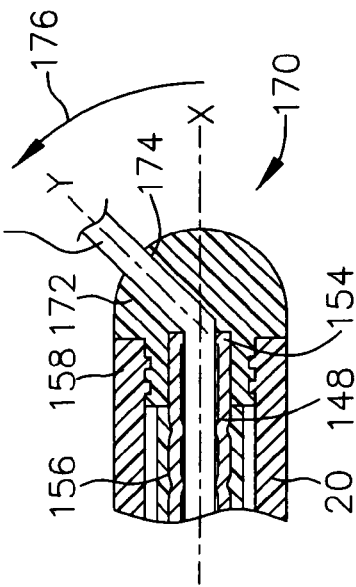
FIG. 14
FIG. 15

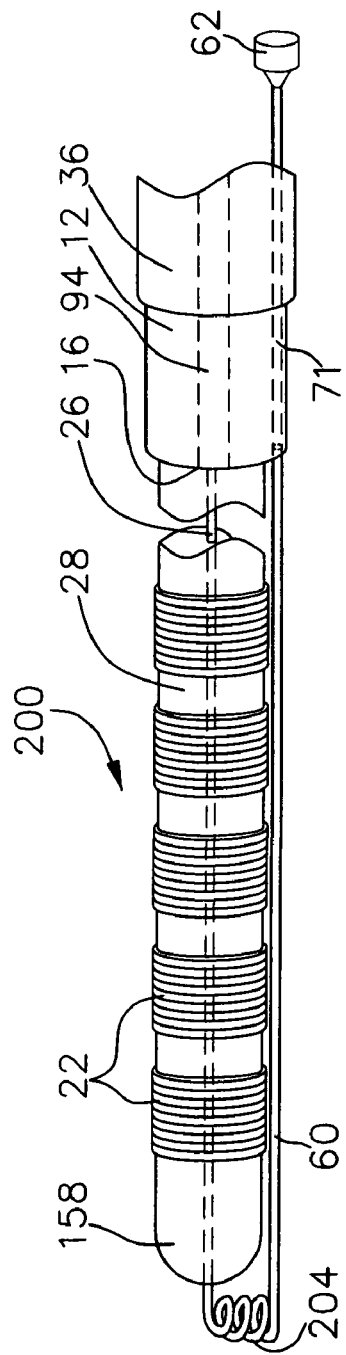
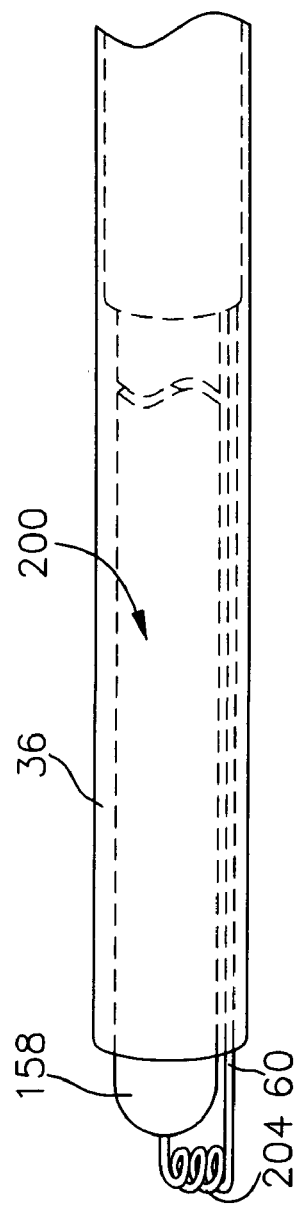

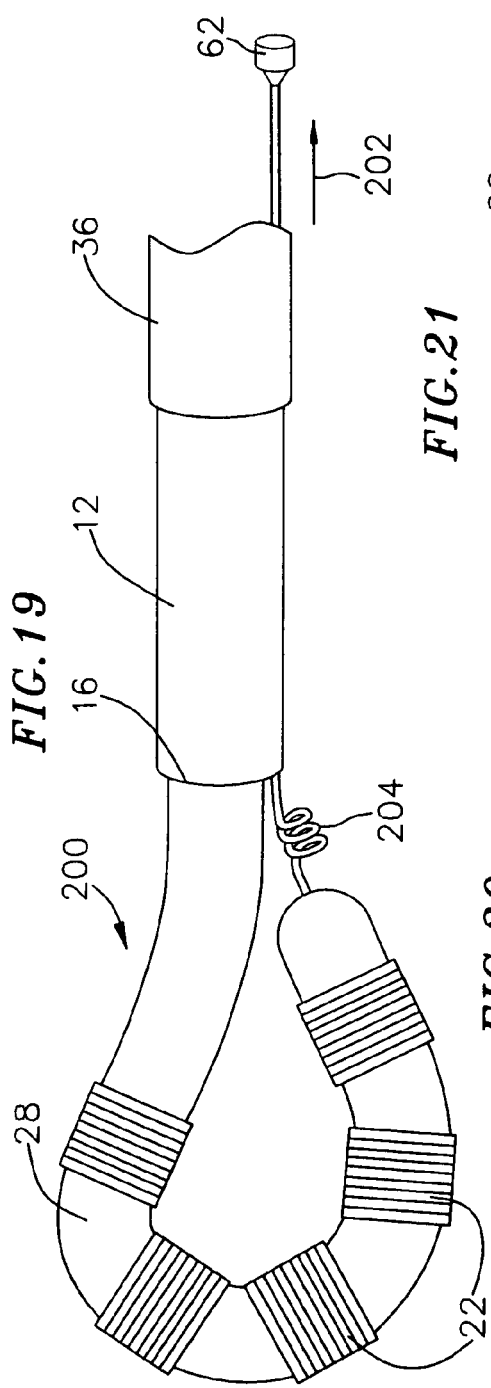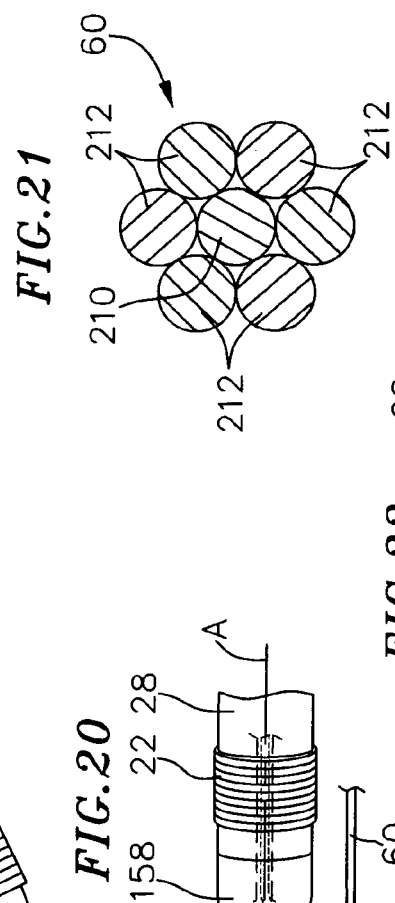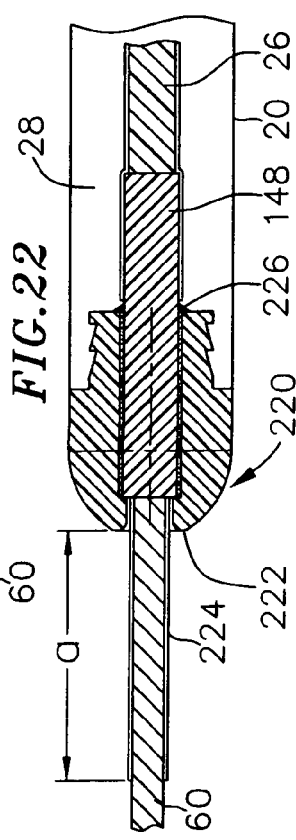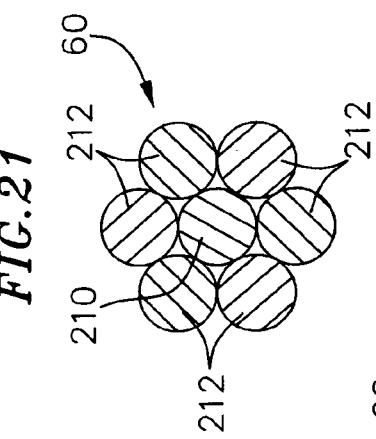

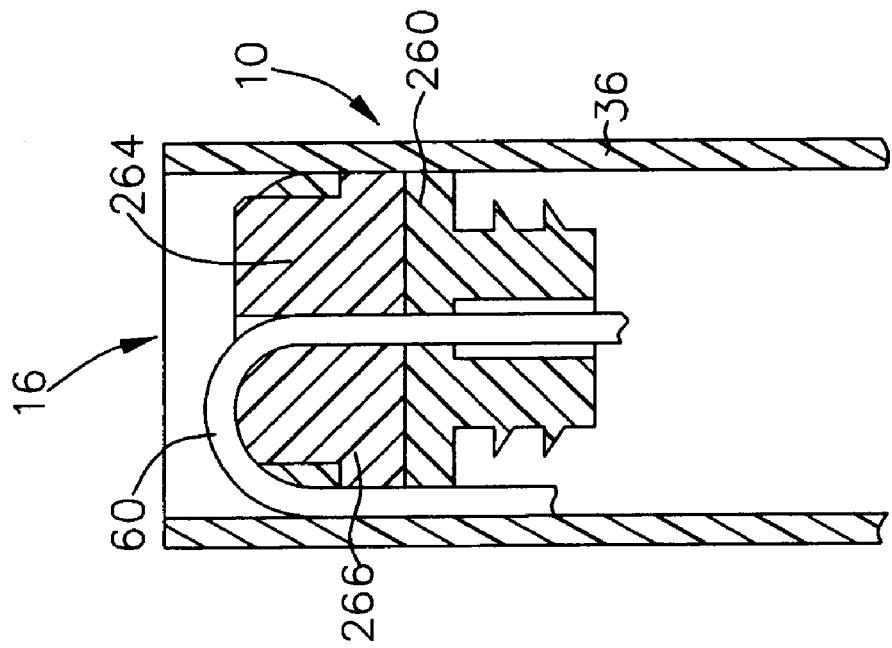
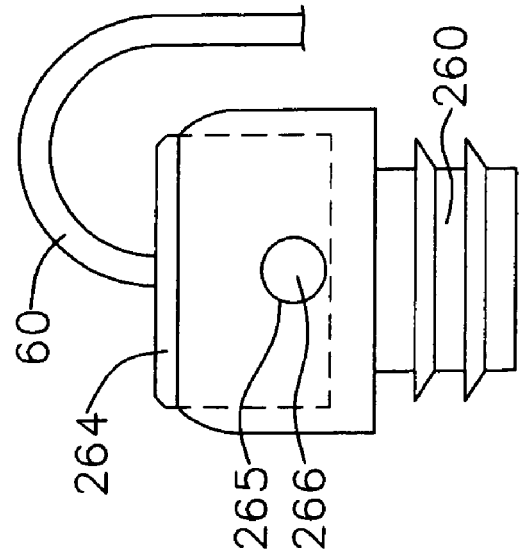
FIG.26B
FIG.26A

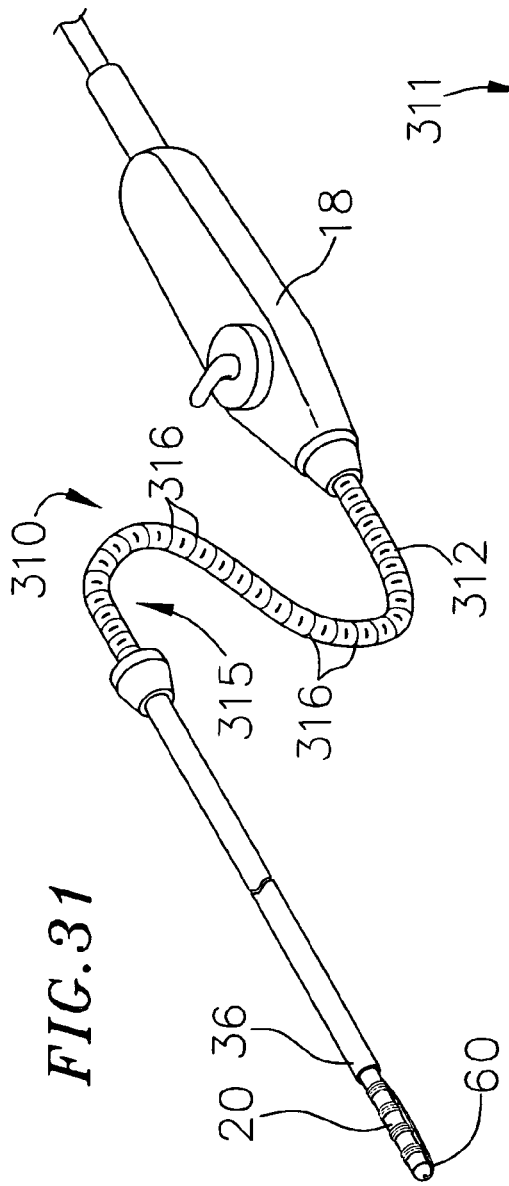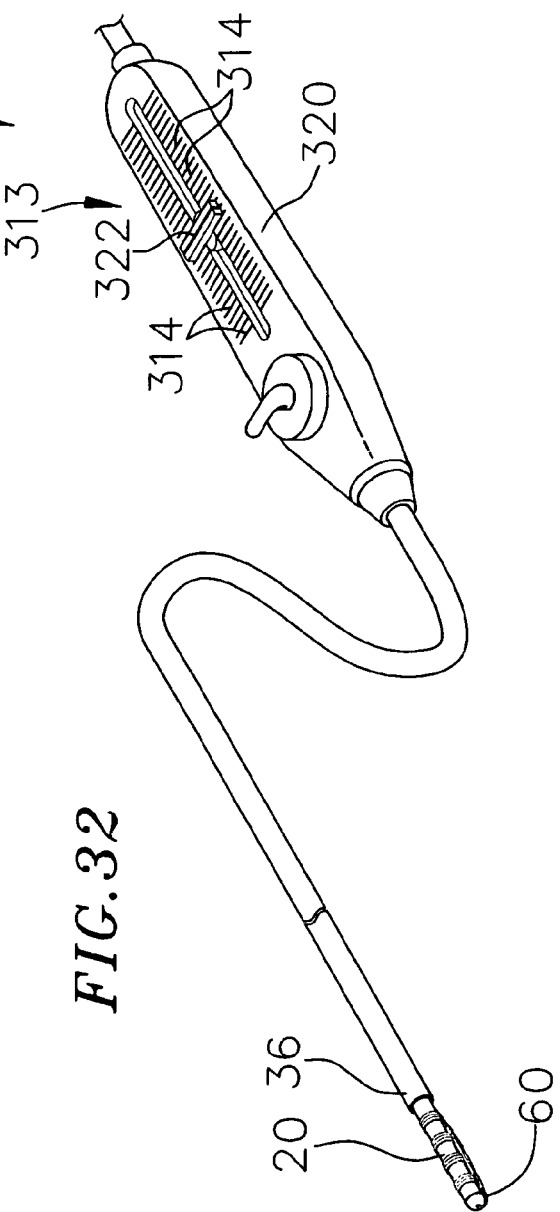

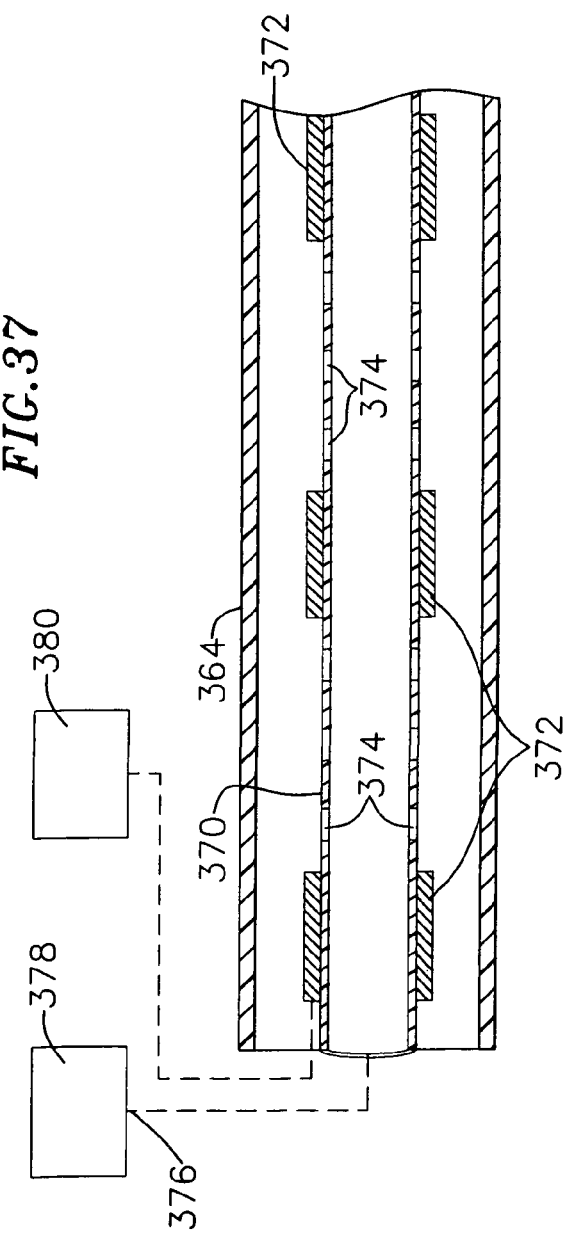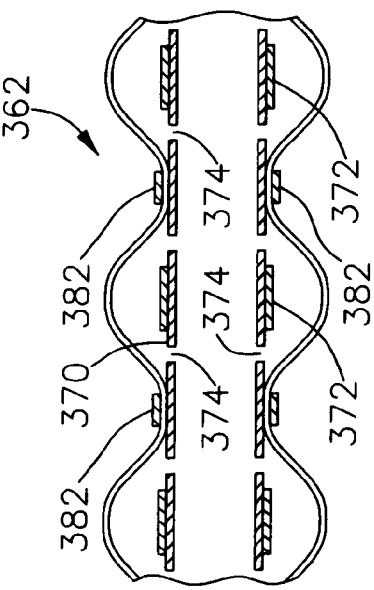

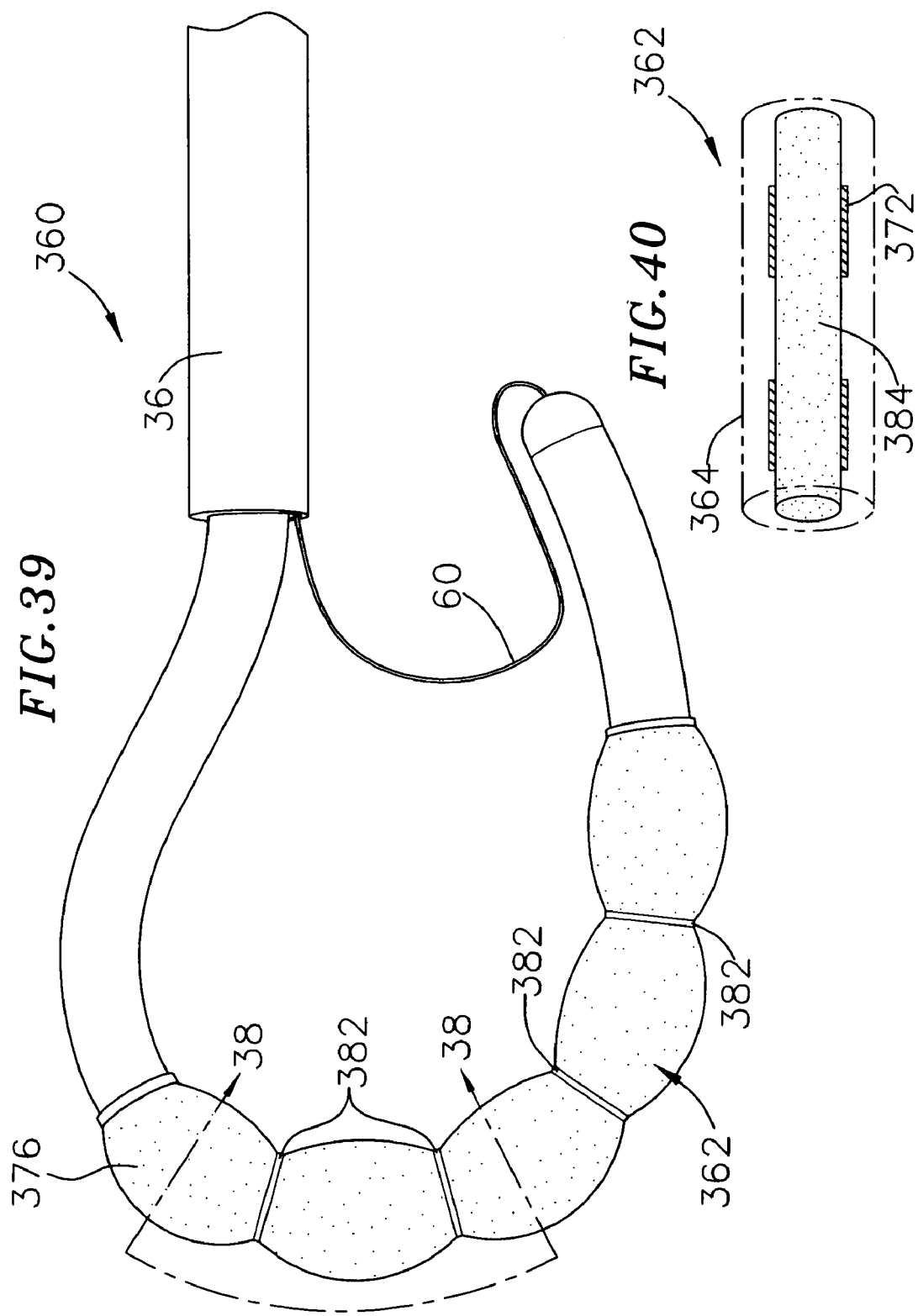

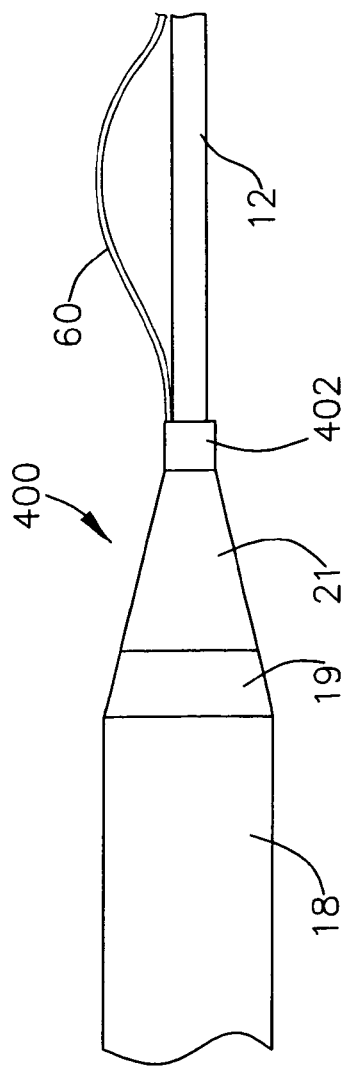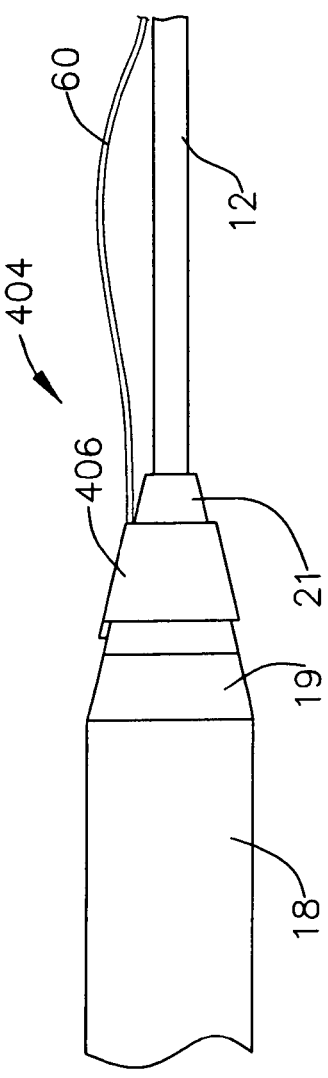

CATHETER DISTAL ASSEMBLY WITH PULL WIRES

CROSS-REFERENCE TO RELATED APPLICATIONS

This application is a continuation of U.S. application Ser. No. 08/961,374, filed Oct. 30, 1997, now U.S. Pat. No. 6,203,525, which is a continuation-in-part of U.S. application Ser. No. 08/769,856, filed Dec. 19, 1996, now U.S. Pat. No. 6,332,880, which is incorporated herein by reference thereto.

BACKGROUND OF THE INVENTION

1. Field of Invention

The invention generally relates to the field of medical surgical instruments, specifically structures for supporting one or more diagnostic or therapeutic elements in contact with body tissue. In a more particular sense, the invention relates to structures well suited for supporting one or more electrode elements within the heart.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia. The treatment of cardiac arrhythmia requires electrodes capable of creating tissue lesions having a diversity of different geometries and characteristics, depending upon the particular physiology of the arrhythmia to be treated.

For example, it is believed that the treatment of atrial fibrillation and flutter requires the formation of continuous lesions of different lengths and curvilinear shapes in heart tissue. These lesion patterns require the deployment within the heart of flexible ablating elements having multiple ablating regions. The formation of these lesions by ablation can provide the same therapeutic benefits that the complex incision patterns that the surgical maze procedure presently provides, but without invasive, open heart surgery.

The task is made more difficult because heart chambers vary in size from individual to individual. They also vary according to the condition of the patient. One common effect of heart disease is the enlargement of the heart chambers. For example, in a heart experiencing atrial fibrillation, the size of the atrium can be up to three times that of a normal atrium.

A need exists for electrode support structures that can create lesions of different geometries and characteristics, and which can readily adopt to different contours and geometries within a body region, e.g., the heart.

SUMMARY OF THE INVENTION

The invention provides structures for supporting operative therapeutic or diagnostic elements within an interior body region, like the heart. The structures possess the requisite flexibility and maneuverability permitting safe and easy introduction into the body region. Once deployed in the body region, the structures possess the capability to exert force against tissue thereby deforming the tissue resulting in conformance between tissue and elements.

A probe assembly in accordance with one embodiment of the invention includes an outer member including a wall defining an interior bore having a distal end and a proximal end, and an elongate body, defining a distal end, a proximal end and an exterior, carried within the outer member. The distal end of the elongate body includes at least one operative element. The elongate body further includes a flexible spline extending from adjacent the distal end toward the proximal end which has a first stiffness. The assembly also includes a control element defining a distal portion extending into the distal end of the elongate body and operably connected to the flexible spline, and a proximal portion extending along the exterior of the elongate body within the outer member toward the proximal end of the outer member. At least the portion of the control element aligned with the distal end of the elongate body has a second stiffness which is less than the first stiffness.

There are many advantages associated with this embodiment of the present invention. For example, this embodiment is more compact than conventional probes. Additionally, the relatively flexible control element is less likely to cause tissue damage than the control elements in conventional probes.

An assembly in accordance with another embodiment of the present invention includes an elongate catheter body, and a control element defining a distal portion operably connected to the distal portion of the catheter body and a proximal portion associated with, and extending along, the exterior surface of the catheter body to an area adjacent the proximal end of the catheter body. The assembly also includes an apparatus, associated with the catheter body and the control element, that is adapted to secure the control element in predetermined relation to the catheter body.

There are many advantages associated with this embodiment of the present invention. For example, the control element, which is typically a pull wire, is less likely to wrap around the catheter body than is the control element in a conventional device. As a result, when the present assembly is used in conjunction with a sheath, the catheter is less likely to become stuck within the sheath.

A probe assembly in accordance with another embodiment of the invention includes an outer member including a wall defining an interior bore, and an elongate body carried within the outer member. The distal portion of the elongate body includes at least one operative element. The elongate body also includes a flexible spline extending from adjacent the distal end toward the proximal end. The flexible spline defines a first cross-sectional shape over a substantial portion thereof and a second cross-sectional shape over a relatively small portion thereof. The assembly also includes a control element defining a distal portion operably connected to at least one of the distal end and distal portion of the elongate body, and a proximal portion extending along the exterior of the elongate body within the outer member toward the proximal end of the outer member.

There are many advantages associated with this embodiment of the present invention. For example, the second cross-sectional shape may be a relatively flat shape. As compared to conventional probe assemblies, the flat shape provides increased predictability and consistency in the deflection direction of the elongate body and, therefore, better control of the movement of the elongate body. This is especially true when the elongate body is used to form loops.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

FIG. 3A is an enlarged side view of an embodiment of the distal region of the probe shown in FIG. 1;

FIG. 3B is a section view of the embodiment of the distal region shown in FIG. 3A;

FIG. 6 is a side view of an embodiment of the distal region shown in FIG. 3A, with the catheter tube having a pre-bent geometry orthogonal to the looped structure;

FIG. 7 is a side view of an embodiment of the distal region shown in FIG. 6, with the sheath advanced forward to straighten the pre-bent geometry;

FIGS. 9, 10, and 11, are side sectional views, largely diagrammatic, showing an embodiment of the distal region shown in FIG. 1, in which the electrode array is movable;

FIG. 14 is an enlarged cross-sectional view of the distal end portion of the device depicted in FIG. 13;

FIG. 15 is an enlarged cross-sectional view, similar to that shown in FIG. 14, depicting an alternative distal tip embodiment of the present invention;

FIG. 17 is an enlarged side view of an alternative embodiment of the distal region of the probe shown in FIG. 1, with the associated sheath withdrawn and with no rearward force applied to the associated pull wire;

FIG. 18 is an enlarged side view of the distal region of the probe shown in FIG. 17, with the associated sheath advanced;

FIG. 19 is an enlarged side view of distal region of the probe shown in FIG. 17, with the associated sheath withdrawn and with rearward force applied to the associated pull wire to form a looped structure;

FIG. 20 is an enlarged side view of an alternative embodiment of the distal region shown in FIG. 17, with a slotted end connection;

FIG. 21 is a cross sectional view of a pull wire according to the present invention;

FIG. 22 is a side cut away view of an alternate embodiment of a catheter end tip according to the present invention;

FIG. 26A is a side view of another embodiment of a catheter end tip protective plug;

FIG. 26B is a section view showing the catheter end tip protective plug illustrated in FIG. 26A in use;

FIG. 31 is a side view of a probe, like that shown in FIG. 1, that includes indicia for marking the extent of movement of the catheter tube relative to the associated sheath;

FIG. 32 is a side view of an alternative embodiment of a probe, of the type shown in FIG. 1, showing indicia for marking the extent of movement of the catheter tube relative to the associated sheath;

FIG. 37 is a side section view of the porous ablation element taken generally along line 37—37 in FIG. 36;

FIG. 38 is a side section view of an alternative embodiment of the porous ablation element, showing segmented ablation regions, taken generally along line 38—38 in FIG. 39;

FIG. 39 is an exterior side view of the segmented ablation regions shown in section in FIG. 38;

FIG. 40 is a side section view of an alternative embodiment of a porous electrode element of the type shown in FIG. 38;

FIG. 41 is a partial side view of a probe in accordance with another embodiment of the present invention;

FIG. 42 is a partial side view of a probe in accordance with still another embodiment of the present invention;

DETAILED DESCRIPTION OF THE PREFERRED EMBODIMENTS

The following is a detailed description of the best presently known mode of carrying out the invention. This description is not to be taken in a limiting sense, but is made merely for the purpose of illustrating the general principles of the invention. The scope of the invention is defined solely by the appended claims.

This Specification discloses various multiple electrode structures in the context of catheter-based cardiac ablation. That is because the structures are well suited for use in the field of cardiac ablation. Still, it should be appreciated that the disclosed structures are applicable for use in other applications. For example, the various aspects of the invention have application in procedures requiring access to other regions of the body, such as, for example, the prostate, brain, gall bladder, and uterus. The structures are also adaptable for use with systems that are not necessarily catheter-based.

The detailed description of the preferred embodiments is organized as follows:
 I. Probe Structures
 II. Loop Size Marking
 III. Deployment and Use of Multiple Electrode Structures
 IV. Flexible Electrode Structures
 V. Structures For Preventing the Pull Wire From Wrapping Around the Catheter Tube The section titles and overall organization of the present detailed description are for the purpose of convenience only and are not intended to limit the present invention.

I. Probe Structures

Figure 1:
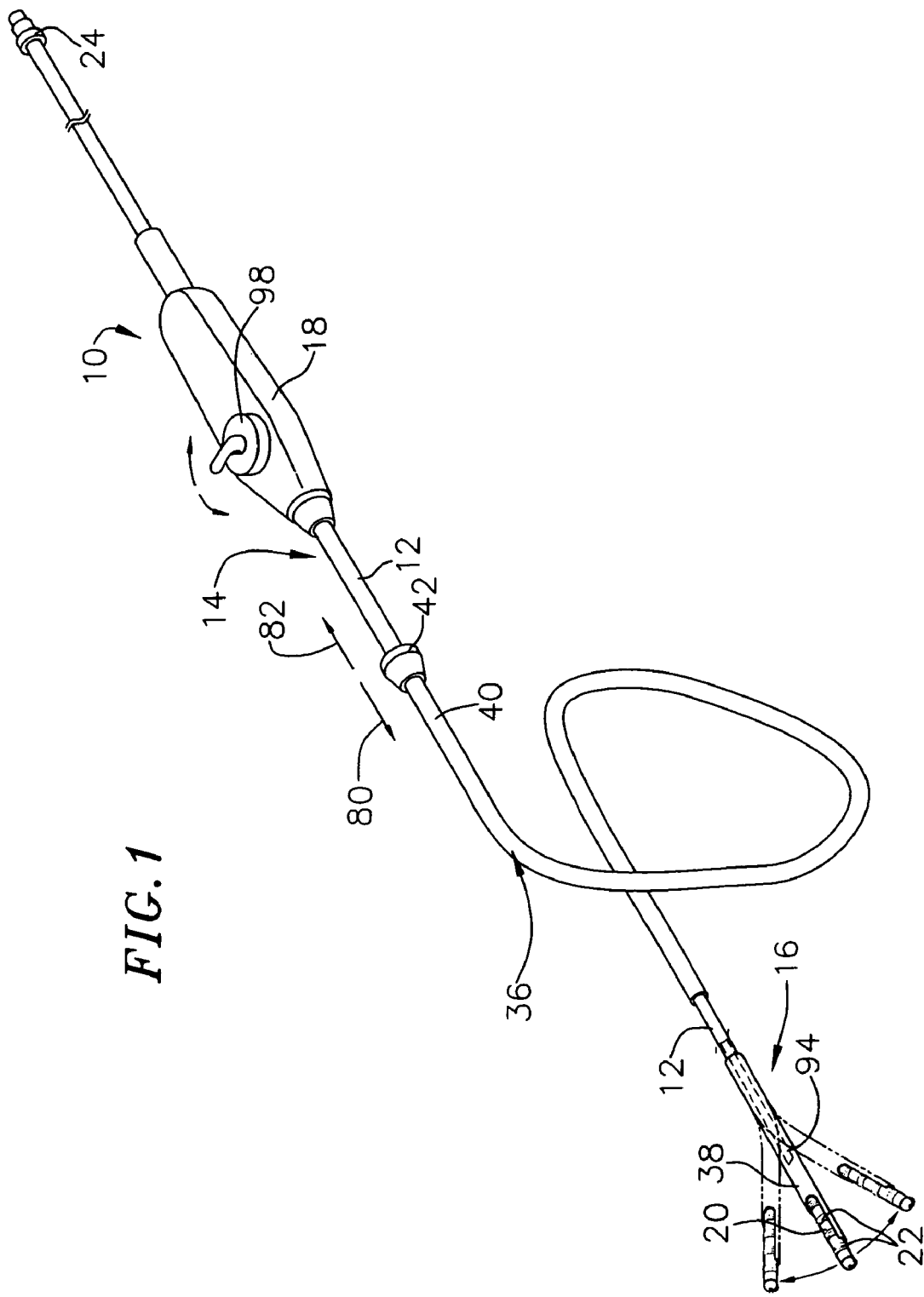
FIG. 1 is a perspective view of a probe, which carries on its distal region a multiple electrode support structure that embodies features of the invention.

FIG. 1 shows a multiple electrode probe 10 having a flexible catheter tube 12 with a proximal end 14 and a distal end 16. The proximal end 14 has an attached handle 18. A multiple electrode structure 20 is attached to the distal end 16 of the catheter tube 12 (see FIG. 2A). It should be noted that the probe 10, as depicted in FIG. 1, is not substantially different from a probe which has been disclosed and claimed in co-pending U.S. application Ser. No. 08/769,856. Differences between the present inventive probe and that previously disclosed will be discussed in relation to subsequent figures, herein.

Electrode elements 22 on the multiple electrode structure 20 can serve different purposes. For example, the electrode elements 22 can be used to sense electrical events in heart tissue. Alternatively, or in addition, the electrode elements 22 can serve to transmit electrical pulses to measure the impedance of heart tissue, to pace heart tissue, or to assess tissue contact. In the illustrated embodiment, the principal use of the electrode elements 22 is to transmit electrical energy, and, more particularly, electromagnetic radio frequency energy, to ablate heart tissue.

The electrode elements 22 are electrically coupled to individual wires (not shown in FIG. 1, but which will be discussed in greater detail below) to conduct ablating energy to them. The wires from the structure 20 are passed in conventional fashion through a lumen in the catheter tube 12 and into the handle 18, where they are electrically coupled to a connector 24 (see FIG. 1). The connector 24 plugs into a source of RF ablation energy (not shown).

Figure 2A:
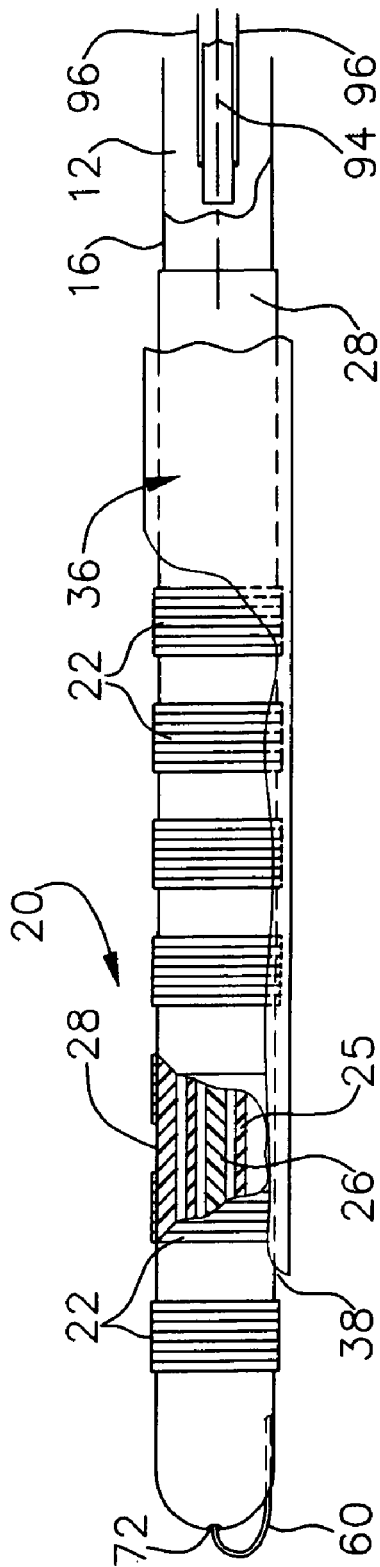
FIG. 2A is an enlarged side view, with portions broken away and in section, of the distal region of the probe shown in FIG. 1.

As FIG. 2A shows, the support structure 20 has a flexible spline 26 (which may comprise a core wire, as will be discussed in more detail hereinafter) surrounded by a flexible, electrically nonconductive distal tubing 28. The multiple electrodes 22 are carried by the distal tubing 28.

The spline 26 is preferably made from resilient, inert wire, like Nickel Titanium (commercially available as Nitinol material) or 17-7 stainless steel. However, resilient injection molded plastic can also be used. Preferably, the spline 26 comprises a thin, rectilinear strip of resilient metal or plastic material. Still, other cross sectional configurations can be used.

The spline 26 can decrease in cross sectional area in a distal direction, by varying, e.g., thickness or width or diameter (if round), to provide variable stiffness along its length. Variable stiffness can also be imparted by composition changes in materials or by different material processing techniques.

Figure 2B:
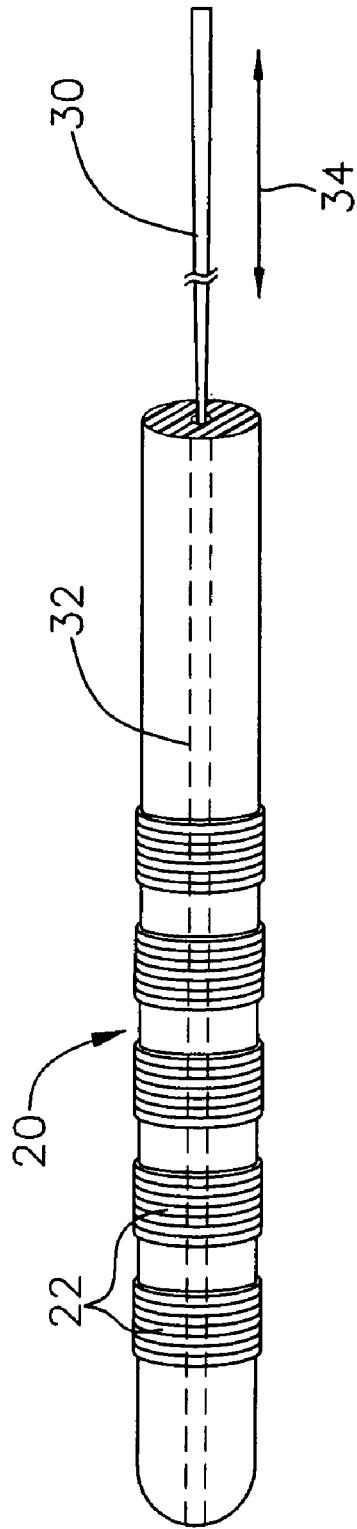
FIG. 2B is a side view of the multiple electrode structure shown in FIG. 1, in which stiffness is varied using a slidable, tapered spline.

As FIG. 2B shows, the stiffness of the support structure 20 can be dynamically varied on the fly by providing a tapered wire 30 that is slidably movable within a lumen 32 in the structure 20. Movement of the tapered wire 30 (arrows 34 in FIG. 2B) adjusts the region of stiffness along the support structure 20 during use.

The distal tubing 28 is made of, for example, a polymeric, electrically nonconductive material, like polyethylene or polyurethane or PEBAX® material (polyether block amide) as, generally, are such comparable components as are discussed herein in relation to other embodiments of the invention. The signal wires for the electrodes 22 preferably extend within the distal tubing 28.

The electrode elements 22 can be assembled in various ways. They can, for example, comprise multiple, generally rigid electrode elements arranged in a spaced apart, segmented relationship along the distal tubing 28. The segmented electrodes 22 can each comprise solid rings of conductive material, like platinum, which makes an interference fit about the distal tubing 28. Alternatively, the electrode segments can comprise a conductive material, like platinum-iridium or gold, coated upon the distal tubing 28 using conventional coating techniques or an ion beam assisted deposition (IBAD) process.

Alternatively, the electrode elements 22 can comprise spaced apart lengths of closely wound, spiral coils wrapped about the distal tubing 28 to form an array of generally flexible electrode elements 22. The coils are made of electrically conducting material, like copper alloy, platinum, or stainless steel, or compositions such as drawn-filled tubing. The electrically conducting material of the coils can be further coated with platinum-iridium or gold to improve its conduction properties and biocompatibility. The electrode elements 22 can also comprise porous materials, which transmit ablation energy through an ionic medium.

The electrode elements 22 can be operated in a uni-polar mode, in which the ablation energy emitted by the electrode elements 22 is returned through an indifferent patch electrode (not shown) externally attached to the skin of the patient. Alternatively, the elements 22 can be operated in a bipolar mode, in which ablation energy emitted by one or more electrode element 22 is returned through another of the electrode elements 22 on the structure 20.

The diameter of the support structure 20 (including the electrode elements 22, flexible distal tubing 28, and the spline 26) can vary from about 2 French to about 10 French.

The support structure 20 must make and maintain intimate contact between the electrode elements 22 and the endocardium or other bodily structure. Furthermore, the support structure 20 must be capable of assuming a relatively low profile for steering and introduction into the body.

To accomplish these objectives, the probe 10 is inserted through a sheath 36 (FIG. 2a). A distal section 38 of the sheath 36 extends about the multiple electrode structure 20 (see FIGS. 1 and 2A). In the embodiment shown in FIG. 1, a proximal section 40 of the sheath 36 terminates short of the handle 18 and includes a raised gripping surface 42. The proximal section 40 also includes a homeostatic valve and side port (not shown) for fluid infusion. Preferably the homeostatic valve locks about the catheter tube 12.

FIGS. 2A and 2B show the structure 20 carrying multiple electrode elements 22 having had added thereto certain elements particular to the illustrated embodiment, as will be discussed hereinafter. As previously discussed herein, the structure 20 is intended, in use, to be carried at the distal end 16 of the flexible catheter tube 12, as a part of the probe 10, as shown in FIG. 1. As has been discussed in relation to FIG. 2, the support structure 20 has the flexible spline 26 surrounded by the flexible, electrically nonconductive distal tubing 28. The multiple electrodes 22 are carried by the distal tubing 28. The distal section 38 of the sheath 36 extends about the multiple electrode structure 20.

In accordance with another aspect of the present invention, and as shown by way of example in FIG. 2A, the support structure 20 may also be provided with a support tube 25 that is located between the distal tubing 28 and the flexible spline 26. The support tube 25 is preferably formed from TEFLON® and is approximately three inches in length. Other materials, such as polyester or silicon, can also be used.

The support tube 25 provides a number of benefits. Most importantly, the support tube 25 prevents the formation of kinks in the distal end of the distal tubing 28 when the support structure 20 is pulled into a relatively tight loop, i.e. a loop with a radius on the order of 0.5 inch. Such kinks can develop between the electrode elements 22, which results in a flat section in the distal tubing 28 between the electrode elements 22. This can lead to the exposure of the edges of the electrode elements 22 and the exposed edges can become caught on the sheath 36 or pinch tissue.

Generally speaking, kinks are less likely to be formed in the proximal end of the distal tubing 28 because there are many more wires passing between the flexible spline 26 and the distal tubing 28 at the proximal end of the distal tubing 28 (such as the wires associated with the electrode elements 22 and the temperature sensors), then there are at the distal end. Absent such wiring and the present support tube 25, there will be a space between the flexible spline 26 and the distal tubing 28 which allows kinks to form when the distal tubing 28 is deflected into a relatively tight loop. The support tube 25 occupies this space, holds the distal tubing 28 open and, therefore, prevents the formation of kinks.

The support tube 25 also increases the stiffness of the support structure 20, thereby helping to ensure electrode/tissue contact.

As shown by way of example in FIG. 3A, a wire 60 extends through the sheath 36 to a stop/handle 62 located proximal to the gripping surface 42 of the sheath 36. Holding the handle 62 stationary, the physician deploys a looped structure 64 (which is the multiple electrode support structure 20 formed into the shape of a loop) by advancing the catheter tube 12 through the sheath 36 (arrow 66). Once the looped structure 64 has been formed, the physician can pull on the wire 60 (arrow 68) to decrease its exposed length beyond the distal sheath section 38, to minimize tissue trauma. Further adjustments to the loop are made by advancing or retracting the catheter tube 12 within the sheath 36. The wire 60 unattached to the sheath 36 allows the physician to interchangeably use the structure 64 with essentially any alternative sheath (not shown).

Alternatively, as FIG. 3B shows, an alternative sheath 36a can include a lumen 70 through which the wire 60 passes. Unlike the embodiment depicted in FIG. 3A, however, the alternative sheath 36a and the wire 60 comprise one integrated unit and cannot be interchanged.

A wire engagement assembly 72 (FIGS. 2A and 3A) provides an anchor point for attaching the distal end of the structure 20 to the wire 60 and will be discussed in greater detail hereinafter.

The catheter tube 12 is slidable within the sheath in a forward and rearward direction, as indicated by arrows 80 and 82 in FIG. 1. By grasping the raised gripping surface 42 at the proximal end of the sheath 36, and pushing the catheter tube 12 in the forward direction (arrow 80) through the sheath 36 (see FIG. 3A), the structure 20, secured to the catheter tube 12 and to the wire 60, and further constrained to the end 38 of the sheath 36, bends outwardly to form the looped structure 64.

The physician can alter the diameter of the looped structure 64 from large to small, by incrementally moving the catheter tube 12 in the forward and rearward directions (arrows 66 and 68) through the sheath 36. In this way, the physician can manipulate the looped structure 64 to achieve the desired degree of contact between tissue and the electrode elements 22.

Figure 4A:
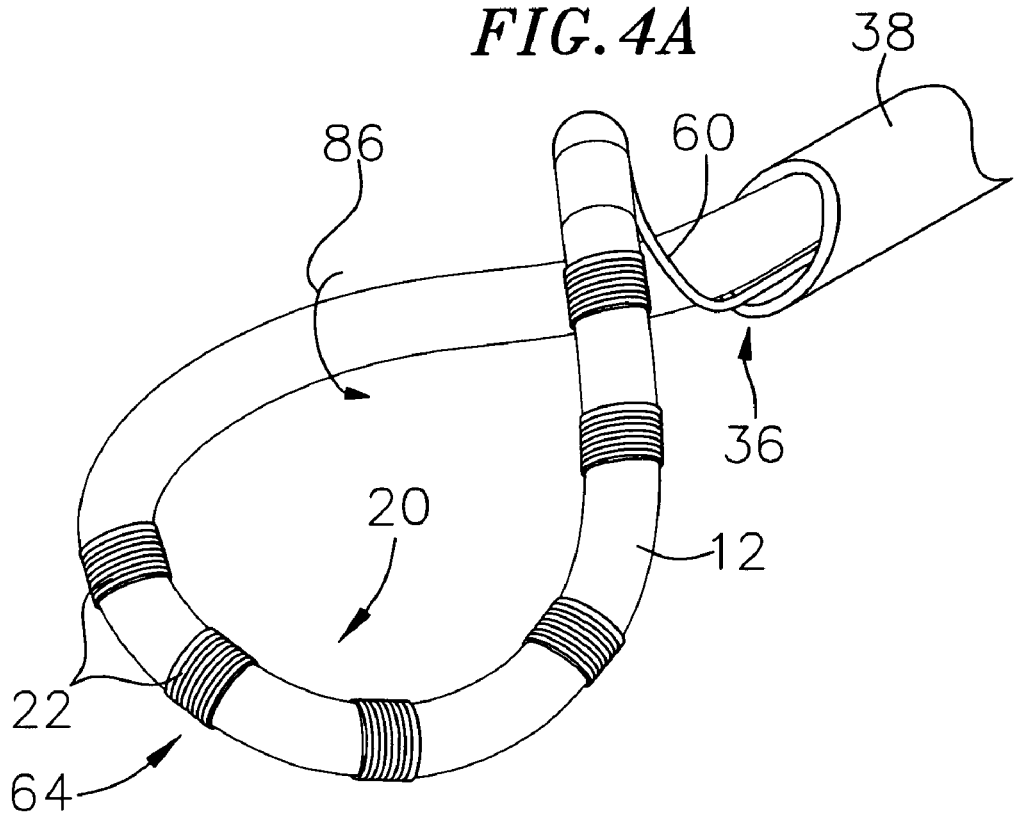
FIG. 4A is a side view of the distal region shown in FIG. 3A, in which the catheter tube is stiffer than the sheath, and in which the catheter tube has been rotated within the sheath and flipped over upon itself.
Figure 4B:
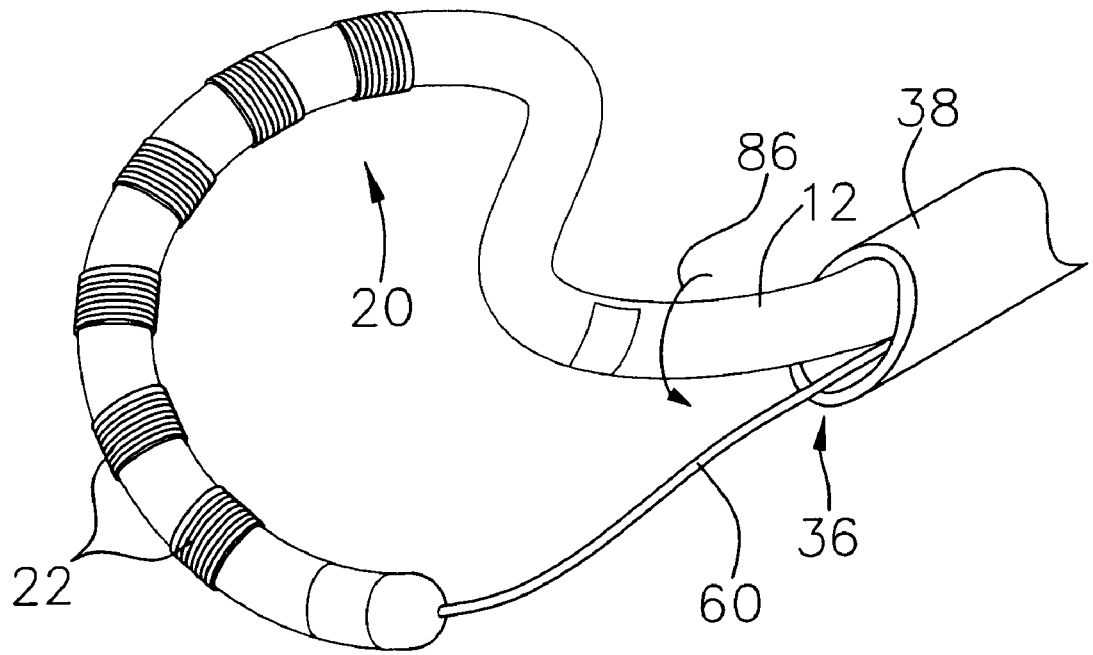
FIG. 4B is a side view of the distal region shown in FIG. 3A, in which the catheter tube is not as stiff as the sheath, and in which the catheter tube has been rotated within the sheath to form an orthogonal bend in the loop.

If desired, the physician can, while grasping the raised gripping surface 42 (FIG. 1), rotate the catheter tube 12 within the sheath 36. As FIG. 4A shows, the relative rotation (arrow 86) which shows rotation of the catheter tube 12, flips the looped structure 64 over upon itself (compare FIGS. 3A and 4A), to place the electrode elements 22 in a different orientation for anatomic location and/or for tissue contact.

By grasping the raised gripping surface 42 and pulling the catheter tube 12 in the rearward direction (arrow 82 of FIG. 1), the physician draws the multiple electrode structure 20 back into the sheath 36, as shown in FIG. 2A. When the multiple electrode structure 20 is housed within the sheath 36, the combination forms a generally straight, low profile geometry for introduction into and out of a targeted body region.

The sheath 36 is made from a material having a greater inherent stiffness than the support structure 20 itself. Preferably, the sheath material is relatively thin (e.g., with a wall thickness of about 0.013 inch) so as not to significantly increase the overall diameter of the distal region of the probe 10 itself. The selected material for the sheath 36 is preferably also lubricious, to reduce friction during relative movement of the catheter tube 12 within the sheath 36. For example, materials made from polytetrafluoroethylene (PTFE) can be used for the sheath 36. Alternatively, a lubricious coating can be applied. Optional features of the distal end of the sheath 36 which are presently preferred by the inventors will be discussed hereinafter in relation to FIG. 3O.

Additional stiffness can be imparted by lining the sheath 36 with a braided material coated with PEBAX® material. Increasing the sheath stiffness imparts a more pronounced D-shape geometry to the formed looped structure 64. Other compositions made from PTFE braided with a stiff outer layer and other lubricious materials can be used. Steps are taken to keep remnants of braided materials away from the exposed distal end 38 of the sheath 36.

Figure 5:
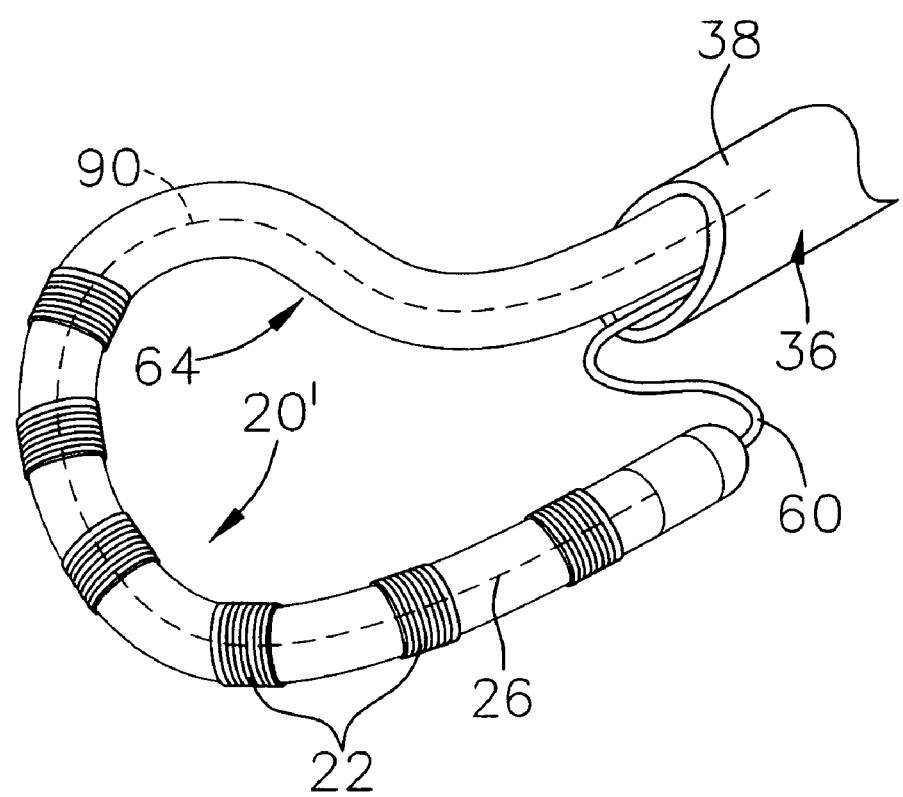
FIG. 5 is a side view of an embodiment of the distal region shown in FIG. 3A, in which a pre-stressed spline within the looped structure alters the geometry of the structure.

As FIG. 5 shows, a region 90 of the spline 26 within the structure 20' away from the electrode elements 22 can be preformed with elastic memory to bow radially away from the electrode elements 22 when advanced from the sheath 36. The radially outward bow of the preformed region 90 forms a more symmetric looped structure 20', in contrast to the more asymmetric tear drop shaped loop 20 shown in FIG. 3A. When in contact with tissue, the preformed, outwardly bowed region 90 generates a back pressure that, in combination with the loop stress maintained by the wire 60, establishes greater contact pressure between electrode elements 22 and tissue.

In FIG. 5, the region 90 is preformed with a generally uniform bend in a single plane. The region 90 can be preformed with complex, serpentine bends along a single plane, or with bends that extend in multiple planes. Further details of representative looped structures having complex, curvilinear geometries will be described in greater detail later.

Additional tissue contact forces can be generated by mounting a bendable spring 94 in the distal end 16 of the catheter tube 12 (see FIG. 2A). One or more steering wires 96 are bonded (e.g., soldered, spot welded, etc.) to the bendable spring 94 extend back to a steering mechanism 98 in the handle 18 (see FIG. 1). Details of steering mechanisms that can be used for this purpose are shown in Lundquist and Thompson U.S. Pat. No. 5,254,088, which is incorporated into this Specification by reference. Operation of the steering mechanism 98 pulls on the steering wires 96 to apply bending forces to the spring 94. Bending of the spring 94 bends the distal end 16 of the catheter tube 12, as shown in phantom lines in FIG. 1.

The plane of bending depends upon the cross section of the spring 94 and the attachment points of the wires 96. If the spring 94 is generally cylindrical in cross section, bending in different planes is possible. If the spring 94 is generally rectilinear in cross section, anisotropic bending occurs perpendicular to the top and bottom surfaces of the spring 94, but not perpendicular to the side surfaces of the spring 94.

Alternatively, or in combination with the manually bendable spring 94, the distal end 16 of the catheter tube 12 can be pre-bent to form a preshaped section 100 (see FIG. 6) generally orthogonal or at some other selected angle to the looped structure 20. In the illustrated embodiment, a preformed wire 102 is secured, e.g., by soldering, spot welding, or with adhesive, to the end 16 of the catheter tube 12. The preformed wire 102 is biased to normally curve. The preformed wire 102 may be made from stainless steel 17/7, nickel titanium, or other elastic material. It may be configured as a wire or as a tube with circular, elliptical, or other cross-sectional geometry.

The wire 102 normally imparts its curve to the catheter tube distal end 16, thereby normally bending the distal end 16 in the direction of the curve. The direction of the normal bend can vary, according to the functional characteristics desired. In the preferred mode of operation, the catheter tube 12 and wire 102 slide (note arrow 106) along the interior of the sheath 104 between a rearward position where the sheath 104 overlies the wire 102 (FIG. 7) and a forward position where the wire 102 is beyond the distal end of the sheath 104 (FIG. 6). The sheath 104 is only moved to reposition the entire system within the body. When the catheter tube 12 is in the rearward position, the sheath 104 retains the catheter tube distal end 16 in a straightened configuration against the normal bias of the wire 102 (FIG. 7). The sheath 104 may include spirally or helically wound fibers to enhance the torsional stiffness of the sheath 104. Upon movement of the catheter tube 12 to its forward position (FIG. 6), the distal end 16 yields to the wire 102 and assumes its normally biased bent position. The slidable sheath 104 may also include a suitable gripping surface (not shown), like the gripping surface 42 of the sheath 36 (note FIG. 1), to enable the physician to prevent movement of the sheath 104 as the catheter tube 12 and wire 102 are moved. In accordance with other modes of operation, the sheath 104 can be moved relative to the catheter tube 12 and wire 102, or ail three elements may be moved, to effect the bending of the distal end 16 shown in FIGS. 6 and 7.

Figure 8A:
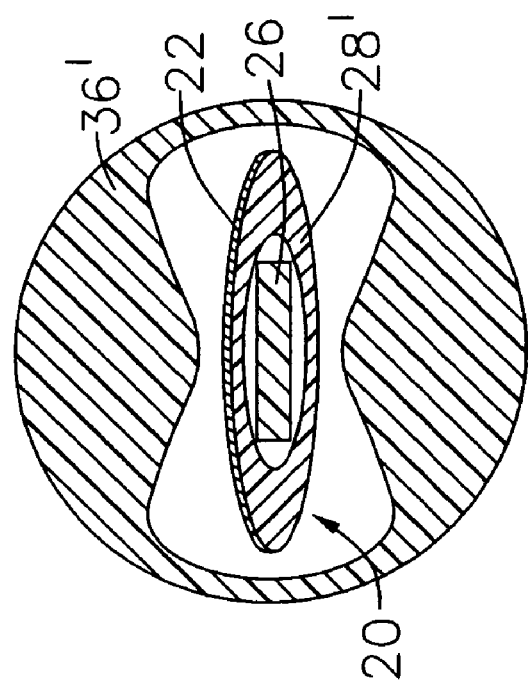
FIG. 8A is a section view of the catheter tube within the sheath, in which the geometries of the sheath and catheter tube are extruded to prevent relative rotation.
Figure 8B:
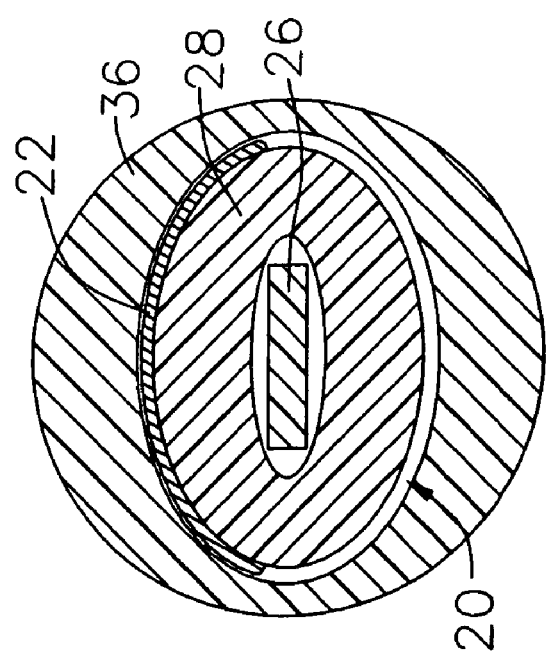
FIG. 8B is a section view of the catheter tube within the sheath, in which the geometries of the sheath and catheter tube are extruded to permit limited relative rotation.

As discussed previously herein, FIG. 4A shows the multiple element structure 20 flipped upon itself by rotation of the looped structure 64 within the sheath 36. The rotation is allowed, because both the electrode structure 20 which makes up the looped structure 64 and sheath 36 possess generally cylindrical cross sections. If it is desired to prevent relative rotation of the structure 20 and catheter tube 12 within the sheath 36, the outer geometry of the structure 20 and the interior geometry of the sheath 36 can be formed as an ellipse, as FIG. 8A shows. The interference (elliptically keyed) arrangement in FIG. 8A prevents rotation of the structure 20 and also provides improved torque response and maintains the electrode elements 22 is a fixed orientation with respect to the sheath 36. By matching the outer geometry of the structure 20 and the interior geometry of the sheath 36 (see FIG. 8B), a prescribed range of relative rotation can be allowed before interference occurs. In FIG. 8B, the elliptical distal tubing 28' will rotate until it contacts the butterfly shaped key way within the sheath 36'.

In at least one preferred embodiment of the present invention, the sheath 36 is made from a material (or combination of materials) having a greater inherent stiffness than the support structure 20. One exemplary sheath construction is a PEBAX® and stainless steel braid composite construction. The selected material for the sheath 36 is preferably also lubricious. For example, materials made from polytetrafluoroethylene (PTFE) can be used for the sheath 36.

The wire 60 comprises a flexible, inert cable constructed from strands of metal wire material, like Nickel Titanium or 17-7 stainless steel. Alternatively, the wire 60 can comprise a flexible, inert stranded or molded plastic material. The wire 60 in FIG. 3A is shown to be round in cross section, although other cross sectional configurations can be used.

Figure 30:
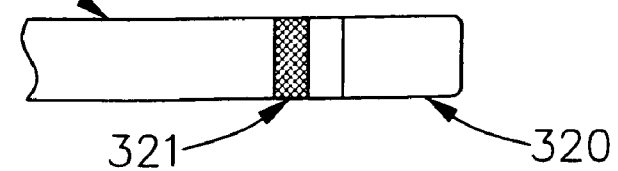
FIG. 30 is a view of the distal end of the catheter sleeve showing optional features thereof.

As shown by way of example in FIG. 30, the distal section 38 of the sheath preferably has a distal end that is perpendicular to the longitudinal axis of the sheath. This makes transseptal introduction into the left atrium easier because there is relatively little opportunity for the distal end of the sheath to catch on the septal wall and tear the septal wall. Alternatively, and as illustrated for example in FIG. 3A, the distal end of the distal sheath section 38 may be cut at an angle and tapered in a transverse direction relative to the longitudinal axis of the sheath 36. The angled linear cut on the distal sheath section 38 might also be a contoured elongated opening, or the like, to make the initiation of the loop formation easier. The angle cut on the sheath 36 helps deploy the structure 20. It is a consideration in the configuration of the distal end of the sheath 38 that the sheath 36 also serves to shield the wire as much as possible from direct surface contact with tissue. The possibility of cutting tissue due to contact with the wire 60 is thereby minimized.

The embodiment shown in schematic form in FIGS. 9, 10, and 11 offers additional options for adjusting the nature and extent of contact between the electrode elements 22 and tissue. As FIG. 9 shows, a flexible spline 124 extends from an external push-pull control 126 through the sheath 130 and is looped back to a point of attachment 128 within the sheath 130. A multiple electrode structure 20, made of an electrically insulated material, is slidable along the spline 124, both within and outside the sheath 130. The multiple electrode structure 20 carries the electrode elements 22. The proximal end of the multiple electrode structure 20 is attached to a push-pull control 132 exposed outside the sheath 130.

By pushing both controls 126 and 132 simultaneously (arrows 134 in FIG. 10), both the spline 124 and the multiple electrode structure 20 are deployed beyond the distal end of the sheath 130. Together, the spline and multiple electrode structure 20 form a looped structure 136 to present the electrode elements 22 for contact with tissue, in much the same way as the multiple electrode structure 20 previously described.

In addition, by holding the spline control 126 stationary while pushing or pulling the control 132 (arrows 134 and 136 in FIG. 11), the physician is able to slide the multiple electrode structure 20 and thus the electrode elements 22 themselves along the spline 124 (as shown by arrows 138 and 140 in FIG. 11). The physician is thereby able to adjustably locate the region and extent of the electrode elements 22 for tissue contact.

Furthermore, by holding the control 132 stationary while pushing or pulling upon the spline control 126, the physician is able to adjust the length of the spline 124 exposed beyond the distal end of the sheath 130. The physician is thereby able to incrementally adjust the radius of curvature in generally the same fashion previously described in the context of FIG. 3.

By pulling both controls 126 and 132 simultaneously (arrows 142 in FIG. 9) both the spline 124 and the multiple electrode structure 20 are moved to a position close to or within the distal end of the sheath 130 for introduction into a body region.

Accordingly, the exemplary arrangement shown in FIGS. 9, 10 and 11 provides a wide range of adjustment options for establishing the desired degree of contact between tissue and the electrode elements 22 carried by the looped structure 136.

Figure 12A:
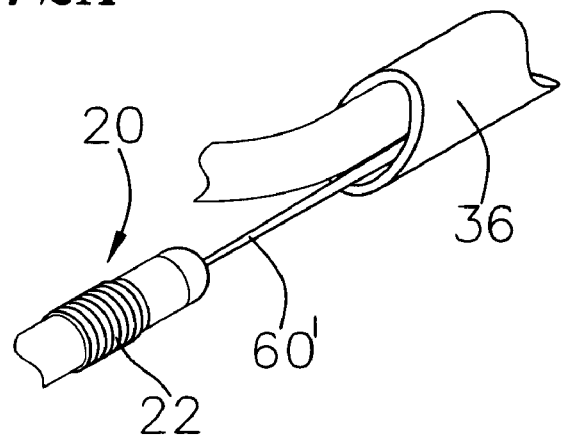
FIGS. 12A and 12B are views of the distal region shown in FIG. 1.

The geometry of the looped structure 64 can be altered by varying the stiffness of the flexible wire 60. As FIG. 12A shows, the flexible wire 60' can be tapered, to provide a cross section that decreases in the distal direction. The tapered cross section provides varying stiffness, which is greatest next to the sheath 36 and decreases with proximity to the distal end of the structure 20.

Figure 12B:
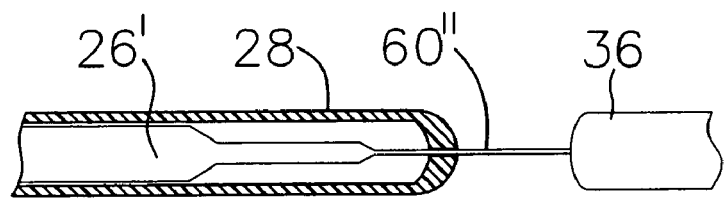

The stiffness can also be changed by changing the thickness of the flexible spline 26 in a step fashion. FIG. 12B shows the flexible spline 26 decreasing in a step fashion leading up to its junction with the wire 60. Changing the thickness of the flexible spline 26 can be done by rolling the wire in steps, or by pressing it, or by chemical etching.

Figure 13:
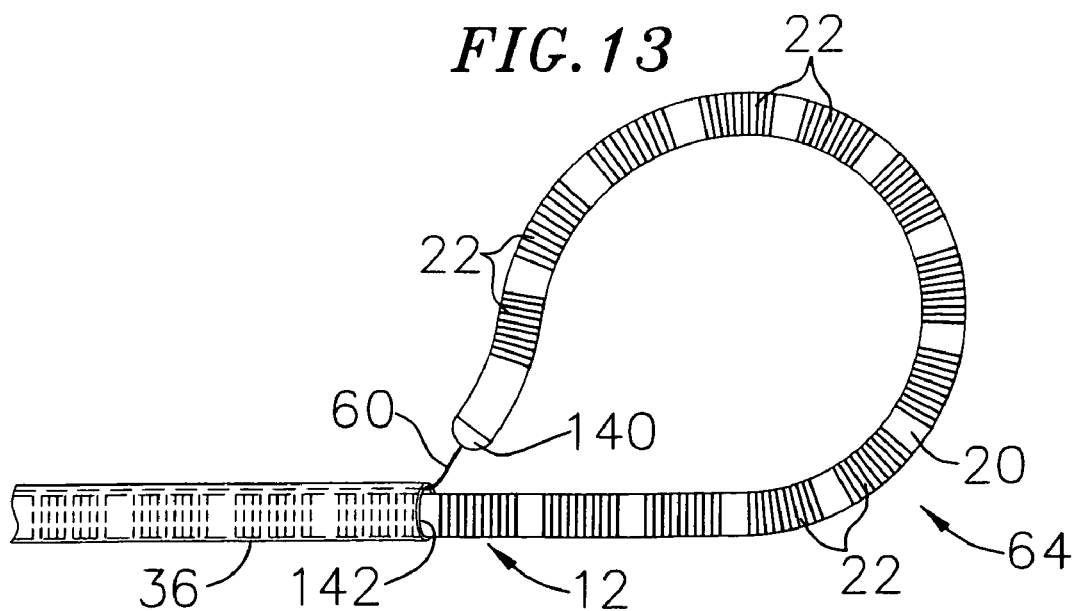
FIG. 13 is an enlarged side view of a pull wire loop configuration of the device depicted in FIG. 1.

Referring now to FIG. 13, there is depicted a side elevation view of the support structure 20 shown in FIG. 3A deformed into a loop configuration 64. In a preferred embodiment, the distal end assembly 20 includes fourteen (14) ablation electrodes 22 (although, as throughout this disclosure, this quantity is not limiting as to the invention) each being approximately 12.5 mm in length. The first of said electrodes 22 is positioned approximately 5 mm from the distal tip 140 of the electrode structure 20, with the remaining electrodes 22 being equally spaced approximately two (2) mm apart down the support structure 20 toward the catheter handle 18 (FIG. 1). Additionally, referring to FIGS. 1 and 3A, to achieve a desired loop configuration of the distal end assembly 20 during normal use of the catheter 10, the user can pull back the sheath 36 relative to the distal assembly 20, causing a desired length of distal assembly 20 to be exposed. Then, holding catheter tube 12 and sheath 36 in place relative to the pull wire 60, the user pulls back on the pull wire handle 62, causing the pull wire 60 to pull back and deflect the distal assembly 20 back toward the sheath end 38 to create the looped structure 64.

Referring now to FIG. 14, there is depicted an enlarged cross-section view of distal assembly/multiple electrode structure 20, showing in detail the pull wire engagement assembly 72 of the present invention. The flexible spline 26 made of solid Nitinol core wire having a preferred diameter approximately of 0.23" is positioned inside of and passes within the length of the catheter tube assembly 12 to the handle 18 (FIG. 1). The proximal end of flexible spline 26 is preferably fixedly engaged to catheter handle 18 by a crimp (not shown) or it is flattened and fastened by other common means (not shown), all as is generally shown in FIG. 1. The distal end 144 of the flexible spline 26 is fixedly engaged in an in-line manner to the distal end 146 of the stranded Nitinol pull wire 60 by utilizing a stainless steel crimp tube 148. The in-line connection of core wire flexible spline 26 and pull wire 60 allows for a reduction in the overall diameter of distal assembly 20 and therefore sheath 36 (FIG. 13) to within clinical norms. This provides a significant clinical advantage over devices having side by side pull wire connections which create a larger diameter device. Pull wire 60 is preferably approximately 0.012 inch to 0.018 inch in diameter providing increased flexibility over a solid wire and thereby reducing the risk of collateral tissue damage during loop manipulation. The pull wire 60 passes through a pull wire bore 150 formed axially through a catheter tip 152, and the tip 152 is fixedly engaged, such as by silver solder, adhesive or spot welding, with a distal end 154 of crimp tube 148. The flexible spline 26 is preferably electrically insulated using a thin walled polyester heat shrink tube 156, and a distal end 158 of structure 20 is fixedly engaged by use of an adhesive to the catheter tip 152.

With further reference to FIG. 14, the flexible spline 26 preferably includes at least one flattened portion 160 which causes the distal tip 140 to deflect in a plane defined by the arrows 162, with a lesser degree of force transmitted from pull wire 60 than would be required without flattened portion 160. The in-line assembly of the flexible spline 26 and pull wire 60, as described above, along with the flattened portion 160 provides increased predictability and consistency in the direction of deflection, and therefore increased control of the movement of the structure 20 and shape of the looped structure 64 during normal use. Additional flattened sections (not shown) of the flexible spline 26 can be included so as to permit the structure 20 to be consistently manipulated into varying loop profile shapes such as ovals, circles and teardrops.

The pull wire engagement assembly 72 may be constructed as follows. First, the flexible spline 26 (which is preferably a solid core wire) is cut to a preferred length of approximately 130 centimeters. Second, an approximately 2 inch portion 160 of the distal portion of flexible spline 26 is flattened to a width of approximately 0.030". Third, the stainless steel crimp tube 148 is fixedly engaged to the round distal end 144 of the flexible spline 26. Fourth, the distal end 146 of an approximately 130 centimeter long stranded Nitinol pull wire 60 is fixedly engaged to the crimp tube 148 that has been engaged to the flexible spline 26. Fifth, the pull wire 60 is positioned through the pull wire bore 150 on the tip 152, and the distal end 154 of the crimp tube 148 is soldered within a crimp sleeve bore 164 formed within the tip 152. Sixth, the polyester heat shrink tube 156 is inserted around the crimp tube 148, enclosing the core and pull wire ends 144 and 146, the flattened portion 160 of the flexible spline 26, and the flexible spline 26 in sufficient length (approximately 12 inches from the tip 152) to insulate the assembly from any possible electrical short circuit of electrical current flowing from lead wires 166 leading from the electrodes 22 to the catheter handle 18 (FIG. 1). Seventh and lastly, the multiple electrode structure 20 is positioned over the crimp tube 148 and fixedly engaged by adhesive to the tip 152. It can be readily understood by one skilled in the art that steps three and four as described above could be switched in sequence without deviating from the spirit and scope of the construction of the distal tip assembly 140 of the invention.

Referring now to FIG. 15, there is shown a second distal tip assembly embodiment 170 of the invention, wherein the tip 152 (FIG. 14) is replaced with an alternative tip 172. Alternative tip 172 is fixedly engaged to the distal end 154 of the crimp tube 148 in the same manner along linear axis X as has previously been described in relation to tip 152 of FIG. 14. However, the alternative tip 172 includes a pull wire bore 174 having an axis Y which intersects the axis X at an angle of approximately 45 degrees, so that pull wire 60 exits tip 172 in the direction of the pull wire bore axis Y. Accordingly, when a pulling force is applied to the pull wire 60, the structure 20 is deformed in the direction of arrow 176 providing increased directional control of the structure 20 in loop formation and electrode positioning.

Figure 16:
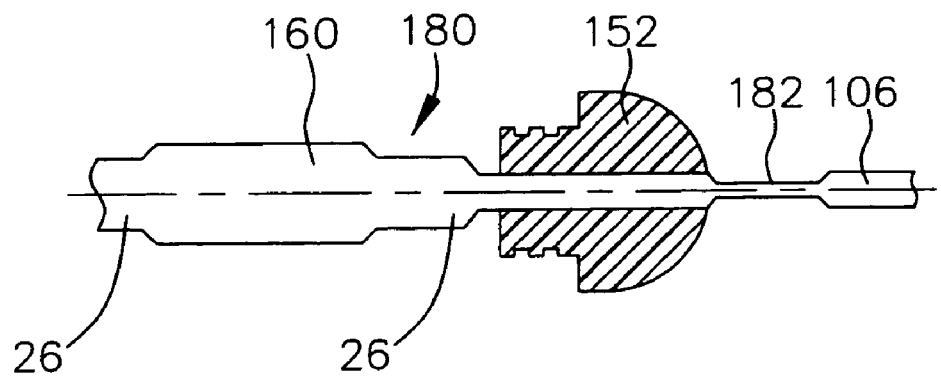
FIG. 16 is a cross-sectional view depicting an alternative, continuous core wire and pull wire embodiment of the present invention.

FIG. 16 depicts yet another embodiment of the present invention wherein the flexible spline 26, pull wire 60 and crimp tube 148 which comprise the distal tip assembly 140 as shown in detail in FIG. 14, is replaced with a unitary core/pull wire 180. Rather than join a stranded pull wire 60 (FIG. 14) to the flexible spline 26, one continuous core wire/pull wire 180 is employed. The diameter of the wire within the structure 20 as described above, can range from approximately 0.020" to 0.050" as required to maintain loop strength (stiffness) of the structure 20 when deployed. A core wire section 182 distal to the flattened section 160 can be reduced in diameter by tapering, centerless grinding, or by flattening portions of the wire. Then, the smaller diameter section 182, ranging from approximately 0.005 inch to 0.012 inch, can be positioned just distal of tip 152 or 172 (FIGS. 14 and 15, respectively) for increased flexibility and durability in the formation of various loop configurations 64.

Figure 16A:
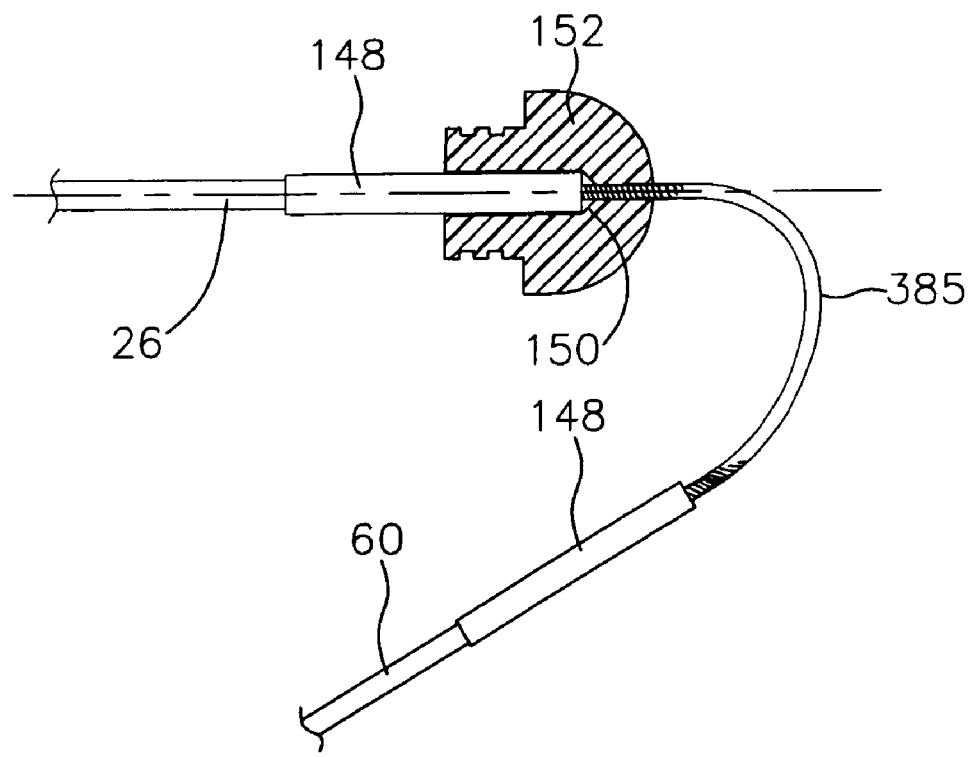
FIG. 16A is yet another alternative embodiment of the present invention.

FIG. 16A depicts yet another alternative embodiment of the present invention. The distal portion of the flexible spline 26 is fixedly engaged in an in-line manner to the proximal end of the strand wire 385 by utilizing the crimp tube 148. As described above with reference to FIG. 14, the strand wire 385 passes through a pull wire bore 150 formed axially through the catheter tip 152. The distal portion of the crimp tube 148 is fixedly engaged to the catheter tip 152 by adhesive or soldering.

The strand wire 385 end farthest from the tip 152 is also fixedly engaged in an in-line manner to the distal end of the flexible wire 60, utilizing a secondary crimp tube 148. The flexible wire 60 is in this case a solid wire which can be pushed or pulled during the manipulation of the catheter distal section 20. In this version, the wire strand 385 is a spring like structure and is flexible enough to reduce the likelihood of fatigue during extreme bending during the introduction and the formation of the loop.

The stranded wire 385, which is also shown in FIG. 21 in more detail, can be made as previously described from Nitinol, 17-7 or resilient plastic.

FIG. 17 shows an alternate embodiment of the present invention having an alternate multiple electrode support structure 200 formed from a spline 26 covered with an electrically insulating distal tubing 28. The electrode elements 22 are carried by the distal tubing 28. The structure 200 is carried at the distal end 16 of a catheter tube 12, and comprises the distal part of a probe 10, in the manner shown in FIG. 1. In these respects, the structure 200 is like the structure 20, previously described, and the same materials as previously described can be used in making the structure 200.

The sheath 36 is intended to be held stationary while the catheter tube 12 is moved to deploy the structure 200. Movement of the catheter tube 12 moves the structure 200 between a rearward position (FIG. 18), where the sheath 36 covers the structure 200 for introduction into a body region, and a forward position (FIGS. 17 and 19), where the structure 200 is exposed for use. The sheath 36 will be moved only to reposition the entire apparatus within the body. Alternatively, the sheath 36 may be moved relative to the catheter tube 12, or the sheath 36 and catheter tube 12 may both be moved, to achieve the same results.

A pull wire 60 extends from the distal end 158 of the structure 200. In the illustrated embodiment, the pull wire 60 is an extension of the spline 26, thereby eliminating the need for an additional distal hub component to join the wire 60 to the distal structure end 158, although the alternative means for attachment of the wire 60 to the spline 26 would be applicable to this present embodiment, as well.

In the presently described embodiment, the catheter tube 12 includes an interior lumen 71, which accommodates sliding passage of the pull wire 60. The pull wire 60 passes through the lumen 71 to an accessible push-pull control stop/handle 62, e.g., mounted on a handle 18 as shown in FIG. 1. When the structure 200 is free of the rearwardly withdrawn sheath 36, the physician pulls back on the wire 60 (arrow 202 in FIG. 19) to bend the structure 200 into a loop.

As FIGS. 17 and 19 show, the wire 60 may optionally include a preformed region 204 adjacent to the distal structure end 158, wound into one or more loops, forming a spring. The region 204 imparts a spring characteristic to the wire 60 when bending the structure 200 into a loop. The region 204 mediates against extreme bending or buckling of the wire 60 during formation of a loop in the structure 200. The region 204 thereby reduces the likelihood of fatigue failure arising after numerous flex cycles.

FIG. 20 shows an alternative embodiment for the structure 200. In this embodiment, the distal structure end 158 includes a slotted passage 206, which extends across the distal structure end 158. In FIG. 20, the slotted passage 206 extends transverse of the longitudinal axis "A" of the structure 200. Alternatively, the slotted passage 206 could extend at other angles relative to the main axis.

Unlike the embodiment shown in FIGS. 17 to 19, the wire 60 in FIG. 20 is not an extension of the spline 26 of the structure 200. Instead, the wire 60 comprises a separate element, which carries a ball 208 at its distal end. The ball 208 is engaged for sliding movement within the slotted passage 206. The ball 208 also allows rotation of the wire 60 relative to the structure 200. The ball 208 and slotted passage 206 form a sliding joint, which, like the spring region 204 of the embodiment shown in FIGS. 17 to 19, reduces the likelihood of fatigue failure arising after numerous flex cycles.

As before described in the context of the structure 20, additional tissue contact forces between the structure 200 and tissue can be generated by mounting a bendable spring 94 in the distal end 16 of the catheter tube (see FIG. 17). Alternatively, or in combination with the manually bendable spring 94, the distal end 16 of the catheter tube 12 can be pre-bent to form a preshaped section generally orthogonal or at some other selected angle to the loop formed by the structure 200.

FIG. 21 is a cross sectional view of one embodiment of the pull wire 60. The pull wire 60 of this embodiment has a central strand 210 and a plurality (six in this example) of surrounding strands 212. In this embodiment, the surrounding strands 212 are twisted, although a linear, or a braided construction would also be possible. The pull wire 60 has been successfully constructed with each of the strands 210 and 212 being made from the materials previously described herein in relation to the pull wire 60. The central strand 210 of the pull wire 60 may, alternatively, be made from platinum. In this embodiment, the diameter of each of the strands 210 and 212 is 0.004 to 0.010 inch, and the approximate total diameter of the stranded pull wire 60 is 0.012 to 0.018 inch. The pull wire 60 may also be formed from a monofilament fiber, such as KEVLAR® or nylon, or a multiple filament fiber. Such fibers may be arranged in the central strand/surrounding strands configuration discussed above, or may simply be a single mono (or multiple) filament strand.

The inventors herein have determined that there may be some instances where it is desirable to reduce the stress that the pull wire 60 will experience during use as well as the likelihood that the pull wire will fray or break due to fatigue at the point where the pull wire 60 exits the catheter tip. A variety of exemplary stress-reducing structures are illustrated in FIGS. 22–27.

FIG. 22 is a side cross sectional view of an alternate catheter tip 220 which is, in many respects, similar to the catheter tip 152 previously discussed herein in relation to the embodiment depicted in FIG. 14. Shown also in the view of FIG. 22 are the flexible spline 26, the pull wire 60, and the crimp tube 148. As can be seen in the view of FIG. 22, unlike embodiments previously discussed herein, the alternate catheter tip has a rounded nose portion 222. The rounded nose portion 222 reduces the stress, as compared to a more squared nose portion, that the pull wire 60 will experience when it is pulled distally back along the catheter tube 12. It should be noted that, in the exemplary embodiment shown in FIG. 22, the crimp tube 148 is affixed to the catheter tip 220 by solder 226.

Also, as can be seen in the view of FIG. 22, an optional protective sleeve 224 may be added to the preferred embodiment which includes the tip 220 having the rounded nose portion 222. The sleeve 224, which is formed from conventional polyester shrink tubing or other types of tubing such as TEFLON® tubing, covers that portion of the pull wire 60 which might be susceptible to wear at the junction of the pull wire 60 and the catheter tip 220. Preferably, the length of the protective sleeve 224 is approximately 1.0 inch, although shorter protective sleeves have been found to perform adequately.

In accordance with another exemplary embodiment of the invention, the protective sleeve 224 may also be used with a catheter tip, such as the catheter tip 152 shown in FIG. 14, to prevent fatigue failure.

Figure 23:
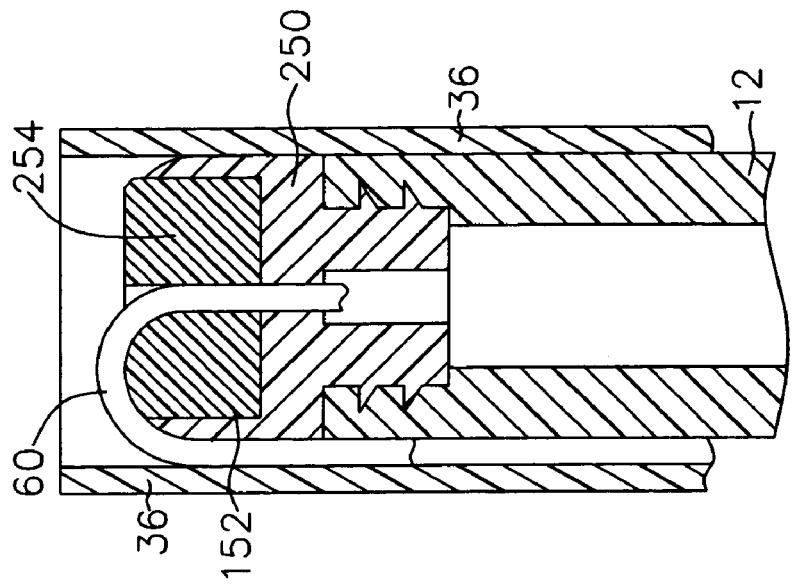
FIG. 23 is a side cut away view of a catheter end tip such as has been described in relation to FIG. 1, showing a stress point thereon.
Figure 24:
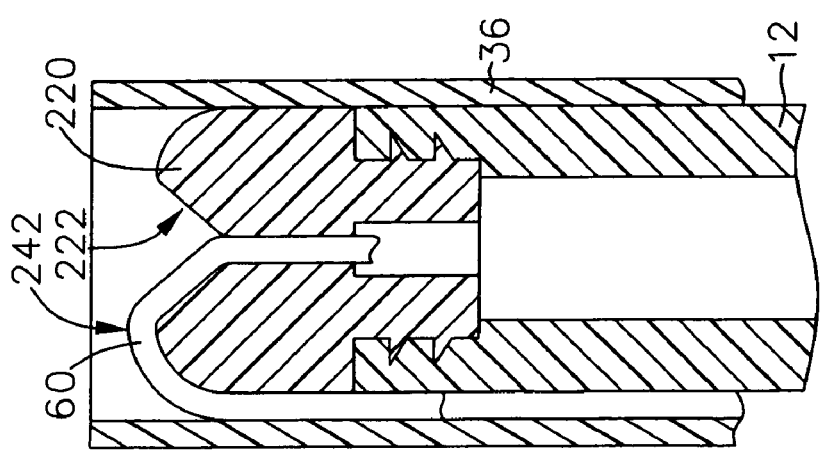
FIG. 24 is a side cut away view of a catheter end tip such as has been described in relation to FIG. 22, showing a stress point thereon.

Further regarding the alternate catheter tip 220 shown in FIG. 22, the inventors have found that the shape of the rounded nose portion 222 is a concern. To illustrate this point and by way of comparison, FIG. 23 is a cross sectional view of the catheter tip 152 and surrounding portions of the probe 10 showing a stress point 230 where the pull wire 60 is forced against the tip 152 when the pull wire 60 is retracted fully into the sheath 36. By comparison, FIG. 24 is a side cross sectional view of the alternative catheter tip having the chamfered nose portion 222 as introduced in relation to FIG. 22. It should be noted that, while stress is much relieved by the rounded nose portion 22, a stress point 242 remains in this configuration.

Figure 25:
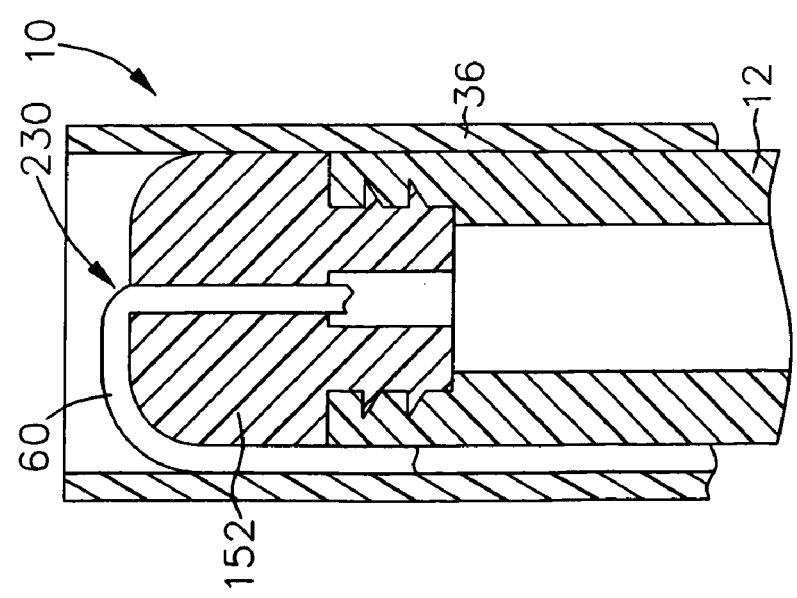
FIG. 25 is a side cut away view of an alternate catheter end tip having a protective plug therein.

FIG. 25 is a side cross sectional view of a second alternate catheter tip 250 having a protective plug 254 inserted in the distal end of the second alternate catheter tip 250. The protective plug 254 is made from an elastomeric material such that stress is alleviated where there otherwise might be a stress point. In the second alternate catheter tip 250, the protective plug 254 is made from polyurethane, although other elastomers such as silicone or other thermoplastic material can also be used. The protective plug 254 is preferably held within the catheter tip 250 with an adhesive.

As shown by way of example in FIGS. 26A and 26B, a third alternate catheter tip 260 has a protective plug 264. Instead of using adhesive, the protective plug 264 is mechanically interlocked with the catheter tip 260. More specifically, the catheter tip 260 includes a pair of holes 265 and the protective plug 264 includes a corresponding pair of radially extending members 266 which are located within the holes 265.

Figure 27:
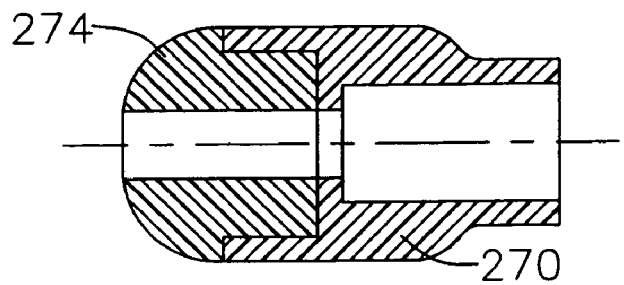
FIG. 27 is a side cut away view of the catheter end tip with another embodiment of a protective plug.

A fourth alternate catheter tip 270, which has a protective plug 274, is shown in FIG. 27. Here, the protective plug 274 extends to the radial edge of the catheter tip 270. It should be noted that the protective plug 274 should be made from a slightly harder (higher durometer) material than the protective plugs 254 and 264.

Figure 28:
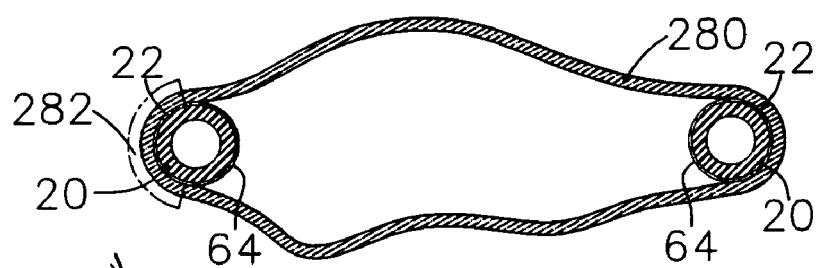
FIG. 28 is a cross sectional view of an atrial wall with the inventive probe 10 deployed therein.

Referring now to FIG. 28, which is a diagrammatic cross sectional view of a portion of atrial wall 280 with the looped structure 64 (as described in relation to FIG. 3) deployed therein. Two of the electrodes 22 of the structure 20 can be seen in the view of FIG. 28 in cross section. It can be seen in the view of FIG. 28 that an ablated portion 282 of the atrial wall 280 (which is that portion of the atrial wall 280 which is in contact with the electrode 22 and will, thus, be ablated by energy dissipated into the atrial wall 280 from the electrode 22) is actually somewhat wider than the diameter of the electrode 22, since the atrial wall 280 is somewhat elastic and tends to conform around the structure 20 when the looped structure 64 is pressed against the atrial wall 280. This is a generally undesirable condition, since it is usually desired to make only narrow contiguous lesions in the atrial wall 280 when tissue is ablated by the electrodes 22.

Figure 29:
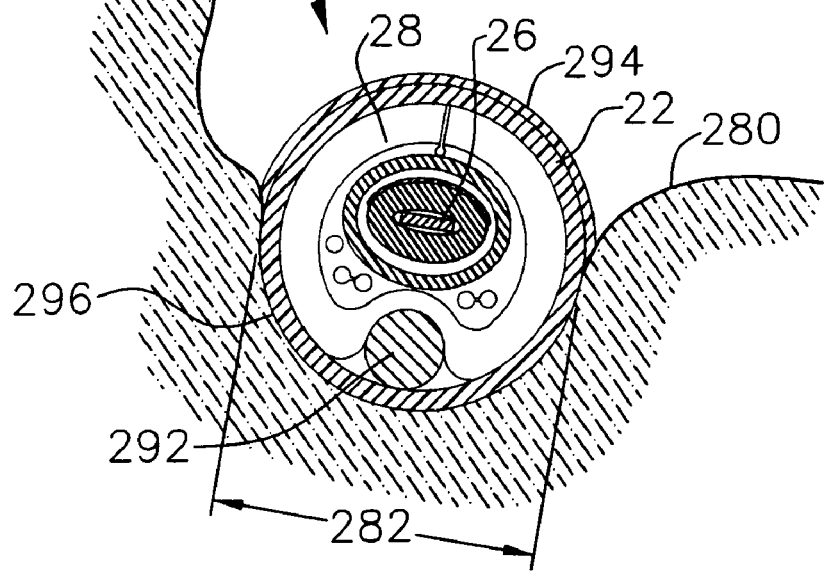
FIG. 29 is a cross sectional view of an electrode structure showing an optional mask thereon.

FIG. 29 is a cross sectional view of a masked electrode structure 290. The masked electrode structure 290 is much like the first introduced electrode structure 20, having a plurality of electrodes 20 (only one of which can be seen in the cross sectional view of FIG. 29) with the flexible spline 26 (a flattened portion thereof being visible in the view of FIG. 29) and distal tubing 28. Also shown in the example of FIG. 29 is a temperature sensor 292 such as may be used in conjunction with the present invention. The masked electrode structure 290 has a mask 294 for protecting a portion of the atrial wall 280 from being heated by the electrode 22 such that the width of the ablated portion 282 of the atrial wall 280 is minimized as desired. It is anticipated by the inventors that an unmasked portion 296 of the electrode 22 will be from approximately 90° to somewhat less than 180° of the cross sectional circumference of the electrodes 22. It is within the scope of the invention that other configurations of the electrodes 22 for minimizing the width of lesions could be used. For example, a resistive electrode element (not shown) could be printed on the multiple electrode structure 20 of FIG. 2a such that the resistive electrode element would cover only a portion of the circumference of the multiple electrode structure.

FIG. 30 is a more detailed view of the distal end of the sheath 38. It should be noted that a sheath tip 320 is preferably made of a soft material. The soft sheath tip 320 can, optionally, be made of a different material than the sheath tubing such that the sheath tip 320 will be softer than the sheath 38. In the preferred embodiment, the soft sheath tip 320 does not have any braid and the distal end thereof is rounded as illustrated in FIG. 30. The soft sheath tip 320 has been found to help decrease the possibility of displacing the electrodes when the multiple electrode structure 20 is brought back into the sheath 38.

As can also be seen in the view of FIG. 30, the distal end of the sheath 38 is preferably provided with radiopaque marker 321 as shown. The radiopaque marker 321 is used to help the clinician orient the distal end of the sheath 38 within the heart. For example, the radiopaque marker 321 is needed if the sheath is placed into the left atrium, through the septal wall. It is very important that the sheath stay in the left atrium while the loop is being used, so that the septum is not unnecessarily stressed. The radiopaque marker 321 near the tip of the sheath 38 will also help identify the location of the catheter tip 152 (FIG. 16) with respect to the distal end of the sheath 38.

Various access techniques can be used to introduce the previously described multiple electrode structures into a desired region of the body. As has been discussed in more detail in the co-pending U.S. application Ser. No. 08/769,856, during introduction, the electrode structure 20 is enclosed in a straightened condition within its associated outer sheath 36 at the end 16 of the catheter tube 12. To enter the right atrium of the heart, the physician directs the catheter tube 12 through a conventional vascular introduce into, e.g., the femoral vein. For entry into the left atrium, the physician can direct the catheter tube 12 through a conventional vascular introducer retrograde through the aortic and mitral valves, or can use a transseptal approach from the right atrium.

Once the distal end 16 of the catheter tube 12 is located within the selected chamber, the physician deploys the structure 20 in the manners previously described.

It should be appreciated that the electrode structure 20 discussed above in the context of intracardiac use, can also be directly applied to the epicardium through conventional thoracotomy or thoracostomy techniques.

The various structures heretofore described, which exhibit compound or orthogonal bends (which will be referred to here collectively as compound bend assemblies) also make it possible to locate the ablation electrodes 22 at any location within a complex body cavity, like the heart. With prior conventional catheter designs, various awkward manipulation techniques were required to position the distal region, such as prolapsing the catheter to form a loop within the atrium, or using anatomical barriers such as the atrial appendage or veins to support one end of the catheter while manipulating the other end, or torquing the catheter body. While these techniques can still be used in association with the compound bend assemblies mentioned above, the compound bend assemblies significantly simplify placing electrode(s) at the desired location and thereafter maintaining intimate contact between the electrode(s) and the tissue surface. The compound bend assemblies make it possible to obtain better tissue contact and to access previously unobtainable sites, especially when positioning multiple electrode arrays.

Compound bend assemblies which provide a proximal curved section orthogonal to the distal steering or loop geometry plane allow the physician to access sites which are otherwise difficult and often impossible to effectively access with conventional catheter configurations, even when using an anatomic barrier as a support structure. For example, to place electrodes between the tricuspid annulus and the cristae terminalis perpendicular to the inferior vena cava and superior vena cava line, the distal tip of a conventional the catheter must be lodged in the right ventricle while the catheter is torqued and looped to contact the anterior wall of the right atrium. Compound bend assemblies which can provide a proximal curved section orthogonal to the distal steering or loop geometry plane greatly simplify positioning of electrodes in this orientation. Compound bend assemblies which provide a proximal curved section orthogonal to the distal steering or loop geometry plane also maintain intimate contact with tissue in this position, so that therapeutic lesions contiguous in the subepicardial plane and extending the desired length, superiorly and/or inferiorly oriented, can be accomplished to organize and help cure atrial fibrillation.

A transseptal approach will most likely be used to create left atrial lesions. In a transseptal approach, an introducing sheath is inserted into the right atrium through the use of a dilator. Once the dilator/sheath combination is placed near the fossa ovalis under fluoroscopic guidance, a needle is inserted through the dilator and is advanced through the fossa ovalis. Once the needle has been confirmed to reside in the left atrium by fluoroscopic observation of radiopaque contrast material injected through the needle lumen, the dilator/sheath combination is advanced over the needle and into the left atrium. At this point, the dilator is removed leaving the sheath in the left atrium.

A left atrial lesion proposed to help cure atrial fibrillation originates on the roof of the left atrium, bisects the pulmonary veins left to right and extends posteriorly to the mitral annulus. Since the lesion described above is perpendicular to the transseptal sheath axis, a catheter which can place the distal steering or loop geometry plane perpendicular to the sheath axis and parallel to the axis of the desired lesion greatly enhances the ability to accurately place the ablation and/or mapping element(s) and ensures intimate tissue contact with the element(s). To create such lesions using conventional catheters requires a retrograde procedure. The catheter is advanced through the femoral artery and aorta, past the aortic valve, into the left ventricle, up through the mitral valve, and into the left atrium. This approach orients the catheter up through the mitral valve. The catheter must then be torqued to orient the steering or loop geometry plane parallel to the stated lesion and its distal region must be looped over the roof of the left atrium to position the ablation and/or mapping element(s) bisecting the left and right pulmonary veins and extending to the mitral annulus.

Preformed guiding sheaths have also been employed to change catheter steering planes. However, preformed guiding sheaths have been observed to straighten in use, making the resulting angle different than the desired angle, depending on the stiffness of the catheter. Furthermore, a guiding sheath requires a larger puncture site for a separate introducing sheath, if the guiding sheath is going to be continuously inserted and removed. Additional transseptal punctures increase the likelihood for complications, such as pericardial effusion and tamponade II. Loop Size Marking FIG. 31 shows a probe 310 having an alternate catheter tube 312 carrying a sheath 36 of the type previously described and shown, e.g., in FIG. 1. The catheter tube 312 includes proximal handle 18 and a distal multiple electrode array 20. The multiple electrode array 20 is deployed as a looped structure from the sheath 36, in the manner previously described and shown. The exemplary probe 310 depicted in FIG. 31 includes indicia 315 on the catheter tube 312 that provides the physician with feedback on the size of the formed looped structure. In FIG. 31, the indicia 315 is in the form of markings 316 on the region of the catheter tube 312 extending through the proximal end of the sheath 36. The markings 316 indicate how much of the catheter tube 312 has been advanced through the sheath 36, which thereby indicates the size of the formed looped structure.

The markings 316 can be made in various ways. They can, for example, be placed on the catheter tube 312 by laser etching, or by printing on the catheter tube 312 using bio-compatible ink, or by the attachment of one or more premarked, heat shrink bands about the catheter tube 312.

In FIG. 32, the sleeve 36 is attached to an alternate handle 320 of the probe 311. The catheter tube is advanced and retracted through the sheath 36 by a push-pull control 322 on the handle 320. In this embodiment, indicia 313, which also provides feedback as to the size of the formed looped structure includes markings 314 on the handle 320 that are arranged along the path of travel of the push-pull control 322. The markings 314, which can be applied to the handle 320, e.g., by laser etching or printing, indicate how much of the catheter tube has been advanced through the sheath 36.

It should be noted that self anchoring techniques, similar to those described in relation to the catheters described and claimed in the co-pending U.S. application Ser. No. 08/769,856, could be readily applied by one skilled in the art to the present invention. The distal end of the structure 20 can be used, as described herein, in conjunction with the anchoring techniques to be discussed hereinafter. Alternative, one skilled in the art will recognize that an elongated portion of the catheter tube 12 could be provided distal to the most distal electrode 22, where such could be used to advantage in conjunction with the below described deployment techniques.

III. Deployment and Use of Multiple Electrode Structures

A. Left Atrium

Figure 33:
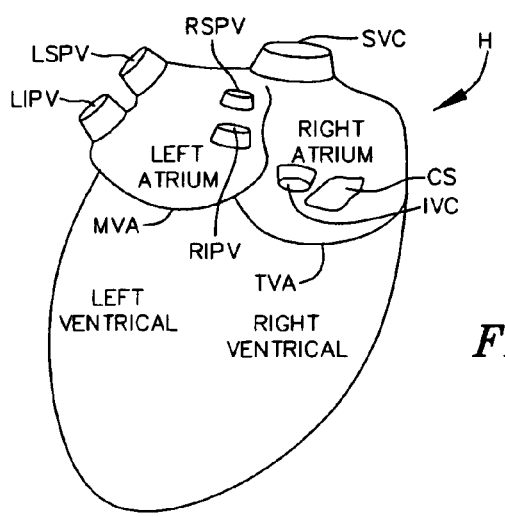
FIG. 33 is a diagrammatic depiction of the location of the major anatomic landmarks for lesion formation in the left atrium.

The multiple electrode structures 20 described above can be deployed into the left atrium to create lesions between the pulmonary veins and the mitral valve annulus. Tissue nearby these anatomic structures are recognized to develop arrhythmia substrates causing atrial fibrillation. Lesions in these tissue regions block reentry paths or destroy active pacemaker sites, and thereby prevent the arrhythmia from occurring. FIG. 33 shows (from outside the heart H) the location of the major anatomic landmarks for lesion formation in the left atrium. The landmarks include the right inferior pulmonary vein (RIPV), the right superior pulmonary vein (RSPV), the left superior pulmonary vein (LSPV), the left inferior pulmonary vein (LIPV); and the mitral valve annulus (MVA). FIGS. 34A to 34D show representative lesion patterns formed inside the left atrium based upon these landmarks.

Figure 34A:
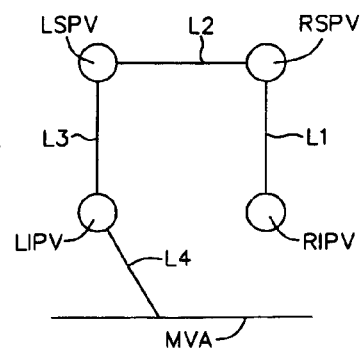
FIGS. 34A to 34D show representative lesion patterns in the left atrium, which rely, at least in part, upon anchoring a structure with respect to a pulmonary vein.

In FIG. 34A, the lesion pattern comprises a first leg L1 between the right inferior pulmonary vein (RIPV) and the right superior pulmonary vein (RSPV); a second leg L2 between the RSPV and the left superior pulmonary vein (LSPV); a third leg L3 between the left superior pulmonary vein (LSPV) and the left inferior pulmonary vein (LIPV); and a fourth leg L4 leading between the LIPV and the mitral valve annulus (MVA).

Figure 34B:
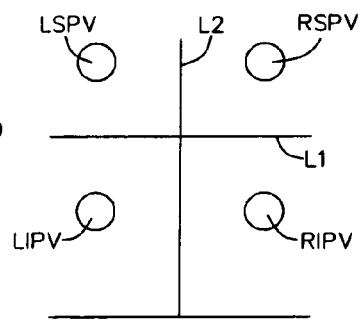

FIG. 34B shows an intersecting lesion pattern comprising horizontal leg L1 extending between the RSPV-LSPV on one side and the RIPV-LIPV on the other size, intersected by vertical leg L2 extending between the RSPV-RIPV on one side and the LSPV-LIPV on the other side. The second leg L2 also extends to the MVA.

Figure 34C:
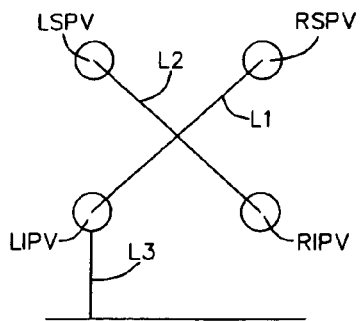

FIG. 34C shows a crisscross-crossing lesion pattern comprising a first leg extending between the RSPV and LIPV; a second leg L2 extending between the LSPV and RIPV; and a third leg L3 extending from the LIPV to the MVA.

Figure 34D:
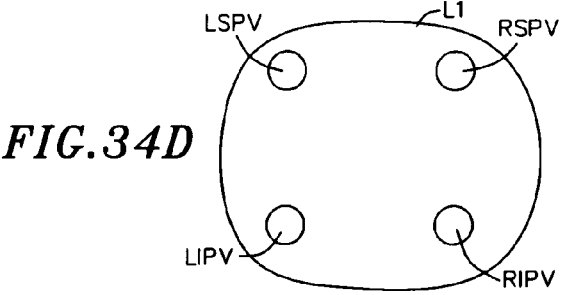

FIG. 34D shows a circular lesion pattern comprising a leg L1 that extends from the LSPV, and encircles to RSPV, RIPV, and LIPV, leading back to the LSPV.

The linear lesion patterns shown in FIGS. 34A, 34B, and 34C can be formed, e.g., using the structure 20 shown in FIGS. 1 and 2, by placing the distal end of the electrode structure 20 in a selected one of the pulmonary veins to stabilize the position of the electrodes 22, and then maneuvering the electrodes 22 to sequentially locate them along the desired legs of the lesion pattern. It may be necessary to relocate the electrodes 22 in a different pulmonary vein to facilitate maneuvering of the electrodes 22 to establish all legs of the pattern.

The circular lesion pattern shown in FIG. 34D can be formed using the distal end of the catheter tube 20. The distal end of the catheter tube 20 is located within a selected one of the pulmonary veins (the LSPV in FIG. 34D), and the looped structure 20 is advanced from the sheath 36 to circumscribe the remaining pulmonary veins. As with other looped structures, the looped structure tend to seek the largest diameter and occupy it. Most of the structures are suitable for being torqued or rotated into other planes and thereby occupy smaller regions. To access the left atrium, any of these structures can be introduced in the manner shown in FIG. 44 through the inferior vena cava (IVC) into the right atrium, and then into the left atrium through a conventional transseptal approach. Alternatively, a retrograde approach can be employed through the aorta into the left ventricle, and then through the mitral valve into the left atrium.

B. Right Atrium

FIG. 33 shows (from outside the heart H) the location of the major anatomic landmarks for lesion formation in the right atrium. These landmarks include the superior vena cava (SVC), the tricuspid valve annulus (TVA), the inferior vena cava (IVC), and the coronary sinus (CS). Tissue nearby these anatomic structures have been identified as developing arrhythmia substrates causing atrial fibrillation. Lesions in these tissue regions block reentry paths or destroy active pacemaker sites and thereby prevent the arrhythmia from occurring.

Figure 35A:
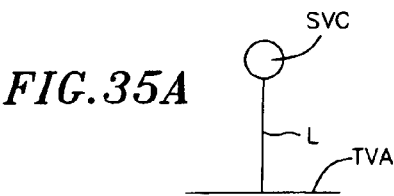
FIGS. 35A to 35C show representative lesion patterns in the right atrium, which rely, at least in part, upon anchoring a structure with respect to the superior vena cava, the inferior vena cava, or the coronary sinus.
Figure 35B:
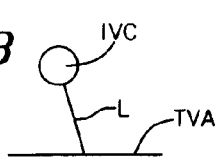
Figure 35C:
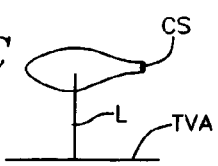

FIGS. 35A to 35C show representative lesion patterns formed inside the right atrium based upon these landmarks. More specifically, FIG. 35A shows a representative lesion pattern L that extends between the superior vena cava (SVC) and the tricuspid valve annulus (TVA). FIG. 35B shows a representative lesion pattern that extends between the interior vena cava (IVC) and the TVA. FIG. 35C shows a representative lesion pattern L that extends between the coronary sinus (CS) and the tricuspid valve annulus (TVA).

The multiple electrode structures described above can be deployed into the right atrium to create these lesions. For example, the structure 20 can be used, by placing the distal tip thereof in the SVC or IVC to stabilize the position of the electrodes 22, and then maneuvering the electrodes to locate them along the desired path of the lesion pattern. Any of these structures can be introduced through the inferior vena cava (IVC) into the right atrium.

C. Surgical Use

Many of the above structures suited for intracardiac deployment, as discussed above, can be directly applied to the epicardium or endocardium through conventional thoracotomy or thoracostomy techniques.

IV. Flexible Electrode Structures

A. Spacing of Electrode Elements

In the illustrated embodiments, the size and spacing of the electrode elements 22 on the various structures can vary.

1. Long Lesion Patterns

For example, the electrode elements 22 can be spaced and sized for creating continuous, long lesion patterns in tissue. Long, continuous lesion patterns are beneficial to the treatment of atrial fibrillation. Such patterns are formed due to additive heating effects, which cause the lesion patterns to span adjacent, spaced apart electrode 22, creating the desired elongated, long geometry.

The additive heating effects occur when the electrode elements 22 are operated simultaneously in a bipolar mode between electrode elements 22. Furthermore, the additive heating effects also arise when the electrode elements 22 are operated simultaneously in a unipolar mode, transmitting energy to an indifferent electrode (not shown).

More particularly, when the spacing between the electrodes 22 is equal to or less than about 3 times the smallest of the diameters of the electrodes 22, the simultaneous emission of energy by the electrodes 22, either bipolar between the segments or unipolar to the indifferent electrode, creates an elongated continuous lesion pattern in the contacted tissue area due to the additive heating effects.

Alternatively, when the spacing between the electrodes 22 along the contacted tissue area is equal to or less than about 2 times the longest of the lengths of the electrodes 22, the simultaneous application of energy by the electrodes 22, either bipolar between electrodes 22 or unipolar to the indifferent electrode, also creates an elongated continuous lesion pattern in the contacted tissue area due to additive heating effects.

Further details of the formation of continuous, long lesion patterns are found in co-pending U.S. patent application Ser. No. 08/287,192, filed Aug. 8, 1994, entitled "Systems and Methods for Forming Elongated Lesion Patterns in Body Tissue Using Straight or Curvilinear Electrode Elements," which is incorporated herein by reference.

Figure 36:
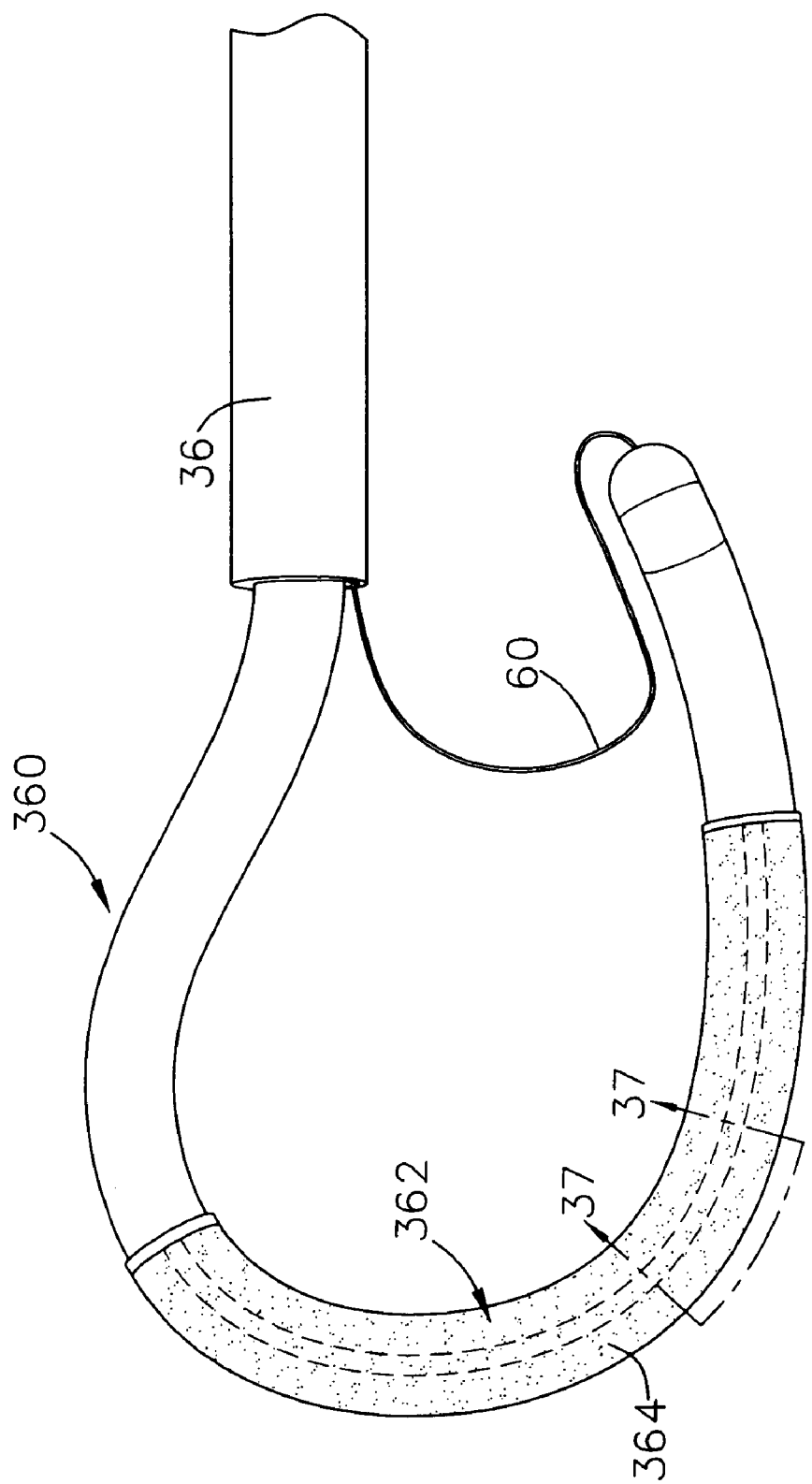
FIG. 36 shows a looped structure of the type shown in FIG. 3A, which carries a porous ablation element.

Alternatively, long continuous lesion patterns can be achieved using an elongated electrode element made from a porous material. By way of illustration, FIG. 36 shows an alternate loop electrode structure 360, similar to that shown in FIG. 2A, but having an electrode body 362 which includes a porous material 364 to transfer ablation energy by ionic transport.

As best shown in FIG. 37, the electrode body 362 includes a center support lumen 370 enveloped by the porous material 364. The lumen 370 carries spaced-apart electrodes 372 along its length. The lumen 370 also includes spaced-apart apertures 374 along its length.

The lumen 370 includes a proximal end 376, which communicates with a source of ionic fluid 378. The lumen 370 conveys the ionic fluid. The ionic fluid passes through the apertures 374 and fills the space between the lumen 370 and the surrounding porous material 364. The fluid also serves to expand the diameter of the structure 360. The structure 360 therefore possesses a low profile geometry, when no fluid is present, for introduction within the targeted body region. Once advanced from the sheath 36 (FIG. 36) and formed into the looped structure 360, fluid can be introduced to expand the structure 360 for use.

The porous material 364 has pores capable of allowing transport of ions contained in the fluid through the material 364 and into contact with tissue. As FIG. 37 also shows, the electrodes 372 are coupled to a source 380 of radio frequency energy. The electrodes 372 transmit the radio frequency energy into the ionic fluid. The ionic fluid establishes an electrically conductive path. The pores of the porous material 364 establish ionic transport of ablation energy from the electrodes 372, through the fluid, to tissue outside the electrode body 362.

Preferably, the fluid possesses a low resistivity to decrease ohmic loses, and thus ohmic heating effects, within the body 362. The composition of the electrically conductive fluid can vary. In the illustrated embodiment, the fluid comprises a hypertonic saline solution, having a sodium chloride concentration at or near saturation, which is about 5% to about 25% weight by volume. Hypertonic saline solution has a low resistivity of only about 5 ohm/cm, compared to blood resistivity of about 150 ohm/cm and myocardial tissue resistivity of about 500 ohm/cm.

Alternatively, the composition of the electrically conductive fluid can comprise a hypertonic potassium chloride solution. This medium, while promoting the desired ionic transfer, requires closer monitoring of the rate at which ionic transport occurs through the pores of the material 364, to prevent potassium overload. When hypertonic potassium chloride solution is used, it is preferred to keep the ionic transport rate below about 10 mEq/min.

Regenerated cellulose membrane materials, typically used for blood oxygenation, dialysis, or ultrafiltration, can be used as the porous material 364. Regenerated cellulose is electrically non-conductive; however, the pores of this material (typically having a diameter smaller than about 0.1 micrometer) allow effective ionic transport in response to the applied RF field. At the same time, the relatively small pores prevent transfer of macromolecules through the material 364, so that pressure driven liquid perfusion is less likely to accompany the ionic transport, unless relatively high pressure conditions develop within the body 362.

Other porous materials can be used as the porous material 364. Candidate materials having pore sizes larger than regenerated cellulose material, such as nylon, polycarbonate, polyvinylidene fluoride (PTFE), polyethersulfone, modified acrylic copolymers, and cellulose acetate, are typically used for blood microfiltration and oxygenation. Porous or microporous materials may also be fabricated by weaving a material (such as nylon, polyester, polyethylene, polypropylene, fluorocarbon, fine diameter stainless steel, or other fiber) into a mesh having the desired pore size and porosity. These materials permit effective passage of ions in response to the applied RF field. However, as many of these materials possess larger pore diameters, pressure driven liquid perfusion, and the attendant transport of macromolecules through the pores, are also more likely to occur at normal inflation pressures for the body 362. Considerations of overall porosity, perfusion rates, and lodgment of blood cells within the pores of the body 362 must be taken more into account as pore size increase.

Low or essentially no liquid perfusion through the porous body 362 is preferred. Limited or essentially no liquid perfusion through the porous body 362 is beneficial for several reasons. First, it limits salt or water overloading, caused by transport of the hypertonic solution into the blood pool. This is especially true, should the hypertonic solution include potassium chloride, as observed above. Furthermore, limited or essentially no liquid perfusion through the porous body 362 allows ionic transport to occur without disruption. When undisturbed by attendant liquid perfusion, ionic transport creates a continuous virtual electrode at the electrode body-tissue interface. The virtual electrode efficiently transfers RF energy without need for an electrically conductive metal surface.

FIGS. 38 and 39 show an embodiment of the porous electrode body 362 which includes spaced-apart external rings 382, which form porous electrode segments 376. It is believed that, as the expanded dimension of the body 362 approaches the dimension of the interior electrodes 372, the need to segment the electrode body 362 diminishes.

Alternatively, as FIG. 40 shows, instead of a lumen 370 within the body, a foam cylinder 384 coupled in communication with the source of ionic fluid 378 could be used to carry the electrodes 372 and perfuse the ionic fluid.

2. Interrupted Lesion Patterns

The electrode elements 22 can be sized and spaced to form interrupted, or segmented lesion patterns. Alternatively, spaced-apart electrode elements 22 which are capable of providing long relatively uninterrupted lesion patterns can be operated with some electrode elements 22 energized and others not, to provide an interrupted lesion pattern.

When the spacing between the electrodes 22 is greater than about 5 times the small st of the diameters of the electrodes 22, the simultaneous emission of energy by the electrodes 22, either bipolar between segments or unipolar to an indifferent electrode, does not generate additive heating effects. Instead, the simultaneous emission of energy by the electrodes 22 creates an elongated segmented, or interrupted, lesion pattern in the contacted tissue area.

Alternatively, when the spacing between the electrodes 22 along the contacted tissue area is greater than about 3 times the longest of the lengths of the electrodes 22, the simultaneous application of energy, either bipolar between electrodes 22 or unipolar to the indifferent electrode, creates an elongated segmented, or interrupted, lesion pattern.

3. Flexibility

When the electrode elements 22 are flexible, each element 22 can be as long as 50 mm. Thus, if desired, a single coil electrode element 22 can extend uninterrupted along the entire length of the support structure. However, a segmented pattern of spaced apart, shorter electrode elements 22 is preferred.

If rigid electrode elements 22 are used, the length of the each electrode segment can vary from about 2 mm to about 10 mm. Using multiple rigid electrode elements 22 longer than about 10 mm each adversely effects the overall flexibility of the element. Generally speaking, adjacent electrode elements 22 having lengths of less than about 2 mm do not consistently form the desired continuous lesion patterns.

4. Temperature Sensing

As previously discussed herein, each electrode element 22 can carry at least one and, preferably, at least two, temperature sensing elements (for example the temperature sensors 292 of FIG. 29). The multiple temperature sensing elements 292 measure temperatures along the length of the electrode element 22. The temperature sensing elements 292 can comprise thermistors or thermocouples. If thermocouples are used, a cold junction can be carried on the same structure as the electrode elements 22.

An external temperature processing element (not shown) receives and analyses the signals from the multiple temperature sensing elements 292 in prescribed ways to govern the application of ablating energy to the electrode element 22. The ablating energy is applied to maintain generally uniform temperature conditions along the length of the element 22.

Further details of the use of multiple temperature sensing elements in tissue ablation can be found in co-pending U.S. patent application Ser. No. 08/286,930, filed Aug. 8, 1994, entitled "Systems and Methods for Controlling Tissue Ablation Using Multiple Temperature Sensing Elements," which is incorporated herein by reference.

V. Structures For Preventing the Pull Wire From Wrapping Around the Catheter Tube In accordance with another aspect of the present invention, the pull wire 60 may be prevented from wrapping around the catheter tube 12 by the exemplary mechanisms illustrated in FIGS. 41–46. Such mechanisms may be used in conjunction with the probes discussed above, or other probes.

As illustrated in FIG. 41, the handle 18 of the exemplary probe 400 is provided with a nose cone 19 and strain relief element 21. In order to prevent the pull wire 60 from wrapping around the catheter tube 12, probe 400 includes an anchoring element 402 which secures the pull wire 60 to the proximal end of the catheter tube 12. Here, the anchoring element 402 is in the form of a length of shrink tubing. Alternatively, the pull wire 60 in the exemplary probe 404 shown in FIG. 42 is secured to the handle 18 by an anchoring element 406, which is also in the form of shrink tubing. The pull wire 60 could also be passed through a lumen (not shown) in the handle 18.

Figure 43:
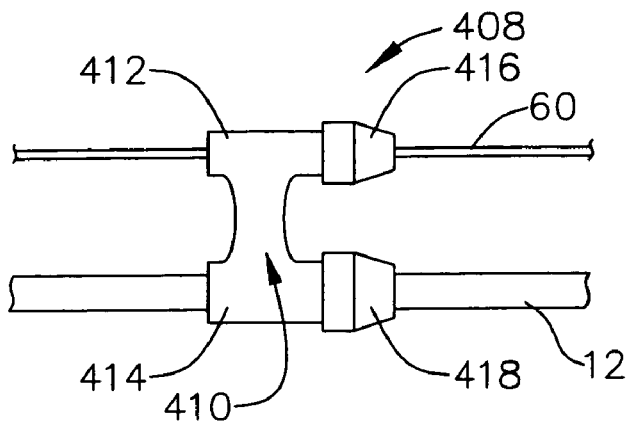
FIG. 43 is side view of a gripping mechanism in accordance with yet another embodiment of the present invention.

Turning to FIG. 43, the pull wire 60 may be secured relative to the catheter shaft 12 by an exemplary gripping mechanism 408 which can be fixed in place on the catheter shaft 12. The gripping mechanism 408 includes a main body 410 and tubular members 412 and 414 which respectively ride on the pull wire 60 and catheter tube 12. The tubular member 412 supports a rotatable vice 416, while the tubular member 414 supports a rotatable vice 418. Preferably, the vices 416 and 418 operate in accordance with the same principles as a pin vice or collet and are operably connected to one another by a mechanical linkage (not shown) to insure that they rotate in unison.

Figure 44:
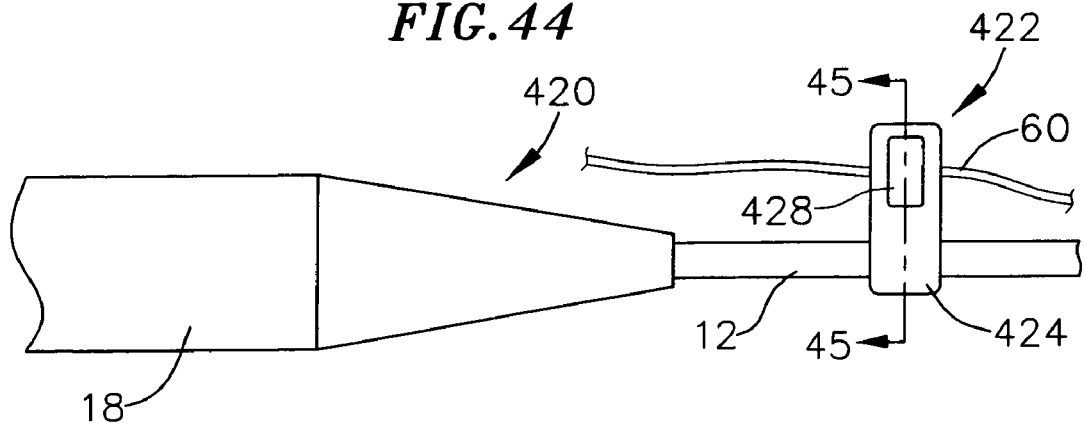
FIG. 44 is a partial side view of a probe in accordance with another embodiment of the present invention.
Figure 45:
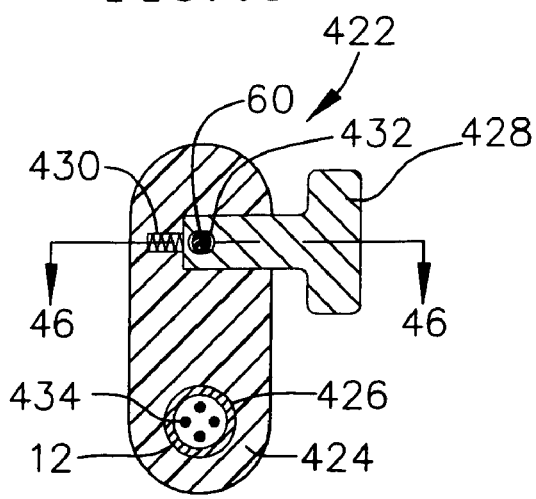
FIG. 45 is a section view taken along line 45—45 in FIG. 44.
Figure 46:
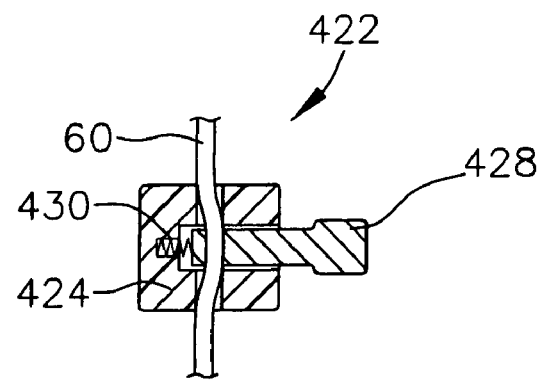
FIG. 46 is a section view taken along line 46—46 in FIG. 45.

Another probe, which is generally represented by reference numeral 420, and which is shown by way of example in FIGS. 44–46, is provided with a gripping mechanism 422. The gripping mechanism 422 includes a main body 424 having an aperture 426 that forms an interference fit with the catheter tube 12 such that the gripping mechanism 422 will not rotate relative to the catheter tube 12. Alternatively, the catheter tube 12 and main body aperture 426 may be keyed by, for example, making the aperture 426 and at least a portion of the catheter tube 12 an oval shape. The pull wire 60 is held in place by a locking button 428 that is biased by a spring 430. The button 428 includes an aperture 432 through which the pull wire 60 passes. The spring 430 biases the button 428 to the orientation best seen in FIG. 46, thereby forcing the side of the aperture 432 against the pull wire 60. Pressing the button 428 will release the pull wire 60 and allow the pull wire 60 to be moved relative to the gripping mechanism 422. It is also noteworthy that wires 434, such as those connected to the electrodes and temperature sensors, are visible in FIG. 45.

The inventors herein have determined that there are many reasons for preventing the pull wire 60 from wrapping around the catheter tube 12. For example, one reason is to prevent the catheter tube 12 from becoming stuck (or locked) within the sheath 36, which hinders the introduction and/or withdrawal of the catheter tube 12 from the sheath 36.

Such locking may occur if the pull wire 60 wraps around the catheter tube 12 many times over a short section of the catheter tube 12. This increases the maximum outer diameter of the catheter (which includes the catheter tube 12, the multiple electrode support structure 20 and the pull wire 60) to a level which prevents movement within the sheath 36. A wrapped pull wire 60 can also catch the electrodes 22 positioned on the deployed loop structure and either dislodge the electrodes 22, or prevent the operator form collapsing the loop.

When the pull wire 60 is secured proximal to the sheath 36 homeostatic valve, rotation of the catheter tube 12 will cause the pull wire 60 to revolve around the catheter tube 12 in the same direction both at the distal end and proximal end of the catheter tube 12. Accordingly, if enough tension were exerted on the pull wire 60 in this configuration, it would straighten within the sheath 36. The catheter tube 12 may be rotated several times and, when withdrawn, the pull wire 60 will straighten, thus decreasing the potential for the pull wire 60 to overlap and catch on the electrodes 22. Additionally, this mechanism enables the operator to observe the direction that the catheter tube 12 has been rotated. Therefore, if the catheter 12 is locked in the sheath 36, the operator can unwind the catheter tube 12 by simply reversing the direction relative to the direction in which the proximal end of the pull wire 60 has revolved around the catheter tube 12. This will straighten the pull wire 60 and unlock the catheter tube 12 from the sheath 36.

Although the present invention has been described in terms of the preferred embodiments above, numerous modifications and/or additions to the above-described preferred embodiments would be readily apparent to one skilled in the art. It is intended that the scope of the present invention extends to all such modifications and/or additions and that the scope of the present invention is limited solely by the claims set forth below.

Additionally, this specification discloses multiple electrode structures in the context of cardiac ablation because the structures are well suited for use in the field of cardiac ablation. Nevertheless, it should be appreciated that the disclosed structures are applicable for use in other applications. For example, various aspects of the invention have applications and procedures concerning other regions of the body such as the prostate, brain, gall bladder and uterus.

We claim:

1. A catheter assembly, comprising:
   a handle including a handle body and a strain relief element;
   an elongate catheter body defining a distal portion, a proximal portion associated with the handle, and a size and flexibility suitable for insertion into a human body; and
   a control element defining a distal portion operably connected to the distal portion of the catheter body and a proximal portion extending along the exterior surface of the catheter body and secured to the strain relief element.

2. A catheter assembly as claimed in claim 1, wherein the control element comprises a pull wire.

3. A catheter assembly as claimed in claim 1, wherein the control element defines a distal end, the catheter body defines a distal end, and the distal end of the control element is associated with the distal end of the catheter body.

4. A catheter assembly as claimed in claim 1, wherein the control element is secured to the strain relief element by a substantially tubular member which surrounds respective portions of the strain relief element and the control element.

5. A catheter assembly as claimed in claim 4, wherein the substantially tubular member comprises heat shrink tubing.

6. A catheter assembly as claimed in claim 1, further comprising:
   a sheath surrounding at least respective portions of the catheter body and control element.

7. A catheter assembly as claimed in claim 1, further comprising:
   a physiological treatment element carried by the distal portion of the elongate catheter body.

8. A catheter assembly as claimed in claim 7, wherein the physiological treatment element comprises a diagnostic element.

9. A catheter assembly as claimed in claim 7, wherein the physiological treatment element comprises a therapeutic element.

10. A catheter assembly as claimed in claim 7, wherein the physiological treatment element comprises an electrode element.

11. A catheter assembly as claimed in claim 10, wherein the electrode element comprises a porous electrode element.

12. A catheter assembly as claimed in claim 10, wherein the electrode element comprises a flexible electrode element.

13. A catheter assembly, comprising:
    a handle including a handle body;
    an elongate catheter body defining a distal portion, a proximal portion associated with the handle, and a size and flexibility suitable for insertion into a human body;
    a control element defining a distal portion operably connected to the distal portion of the catheter body and a proximal portion extending along the exterior surface of the catheter body; and
    an apparatus, located in spaced relation to the handle body, adapted to secure the proximal portion of the control element in predetermined relation to the catheter body.

14. A catheter assembly as claimed in claim 13, wherein the handle includes a strain relief element associated with the handle body and the apparatus includes the strain relief element.

15. A catheter assembly as claimed in claim 14, wherein the apparatus further includes a device that secures the proximal portion of the control element to the strain relief element.

16. A catheter assembly as claimed in claim 15, wherein the device comprises an anchoring element.

17. A catheter assembly as claimed in claim 16, wherein the anchoring element comprises a tube.

18. A catheter assembly as claimed in claim 13, wherein the apparatus covers a region of the proximal portion of the control element and a region of the proximal portion of the catheter body.

19. A catheter assembly as claimed in claim 13, wherein the apparatus comprises an anchoring element that secures the proximal portion of the control element to the proximal portion of the catheter body.

20. A catheter assembly as claimed in claim 19, wherein the anchoring element comprises a tube.

21. A catheter assembly as claimed in claim 13, wherein the control element comprises a pull wire.

22. A catheter assembly as claimed in claim 13, further comprising:
    a sheath surrounding at least respective portions of the catheter body and control element.

23. A catheter assembly as claimed in claim 13, further comprising:

a physiological treatment element carried by the distal portion of the elongate catheter body.

24. A catheter assembly as claimed in claim 23, wherein the physiological treatment element comprises a diagnostic element.

25. A catheter assembly as claimed in claim 23, wherein the physiological treatment element comprises a therapeutic element.

26. A catheter assembly as claimed in claim 23, wherein the physiological treatment element comprises an electrode element.

27. A catheter assembly as claimed in claim 26, wherein the electrode element comprises a porous electrode element.

28. A catheter assembly as claimed in claim 26, wherein the electrode element comprises a flexible electrode element.

* * * * *